(12) United States Patent
Hunt

(10) Patent No.: US 10,980,797 B2
(45) Date of Patent: Apr. 20, 2021

(54) USE OF GLUCOCORTICOID RECEPTOR MODULATORS TO POTENTIATE CHECKPOINT INHIBITORS

(71) Applicant: Corcept Therapeutics Incorporated, Menlo Park, CA (US)

(72) Inventor: Hazel Hunt, West Sussex (GB)

(73) Assignee: Corcept Therapeutics Incorporated, Menlo Park, CA (US)

( * ) Notice: Subject to any disclaimer, the term of this patent is extended or adjusted under 35 U.S.C. 154(b) by 7 days.

(21) Appl. No.: 16/080,617

(22) PCT Filed: Feb. 28, 2017

(86) PCT No.: PCT/US2017/019948
§ 371 (c)(1),
(2) Date: Aug. 28, 2018

(87) PCT Pub. No.: WO2017/151613
PCT Pub. Date: Sep. 8, 2017

(65) Prior Publication Data
US 2019/0083486 A1    Mar. 21, 2019

Related U.S. Application Data

(60) Provisional application No. 62/320,276, filed on Apr. 8, 2016, provisional application No. 62/302,106, filed on Mar. 1, 2016.

(51) Int. Cl.
| | |
|---|---|
| *A61K 31/4745* | (2006.01) |
| *A61K 39/395* | (2006.01) |
| *A61K 31/575* | (2006.01) |
| *A61K 31/444* | (2006.01) |
| *C07K 16/28* | (2006.01) |
| *A61K 45/06* | (2006.01) |
| *A61P 35/00* | (2006.01) |
| *A61K 31/57* | (2006.01) |
| *A61K 39/00* | (2006.01) |

(52) U.S. Cl.
CPC ........ *A61K 31/4745* (2013.01); *A61K 31/444* (2013.01); *A61K 31/57* (2013.01); *A61K 31/575* (2013.01); *A61K 39/3955* (2013.01); *A61K 45/06* (2013.01); *A61P 35/00* (2018.01); *C07K 16/2818* (2013.01); *A61K 2039/505* (2013.01)

(58) Field of Classification Search
CPC .............. A61K 31/4745; A61K 31/575; A61K 31/444; A61K 45/06; A61K 31/57; A61K 39/3955; A61K 2039/505; A61K 31/437; A61K 31/567; A61K 2300/00; C07K 16/2818; A61P 35/00
See application file for complete search history.

(56) References Cited

U.S. PATENT DOCUMENTS

| | | | |
|---|---|---|---|
| 7,928,237 B2 | 4/2011 | Clark et al. | |
| 8,461,172 B2 | 6/2013 | Clark et al. | |
| 8,859,774 B2 | 10/2014 | Hunt et al. | |
| 9,149,485 B2 | 10/2015 | Pan et al. | |
| 10,047,082 B2 | 8/2018 | Hunt et al. | |
| 2012/0238549 A1 | 9/2012 | Cusack et al. | |
| 2014/0341849 A1 | 11/2014 | Pan et al. | |
| 2015/0080389 A1 | 3/2015 | Hunt et al. | |
| 2015/0118244 A1 | 4/2015 | Shahabi et al. | |
| 2015/0346210 A1 | 12/2015 | Nitta et al. | |
| 2018/0064679 A1* | 3/2018 | Pierce | A61K 31/573 |

FOREIGN PATENT DOCUMENTS

| | | |
|---|---|---|
| JP | 2014530812 A | 11/2014 |
| JP | 2015517580 A | 6/2015 |
| WO | 2013039916 A1 | 3/2013 |
| WO | 2013052652 A1 | 4/2013 |
| WO | 2013177559 A2 | 11/2013 |
| WO | 2015061752 A1 | 4/2015 |
| WO | 2015/077414 A1 | 5/2015 |
| WO | 2015070060 A1 | 5/2015 |
| WO | 2015/095811 A2 | 6/2015 |
| WO | 2015100282 A1 | 7/2015 |

OTHER PUBLICATIONS

Iams et al. (My Cancer Genome, pp. 1-5, Nov. 24, 2015).*
(Transl. Lung Cancer Res. 3(6): 408-410, Dec. 2014).*
Of P'eng et al. (Cancer 62: 2134-2138, 1988).*
Sygnature Discovery News (pp. 1 and 2, publically available Jul. 30, 2015).*
Nocentini et al, "A new member of the tumor necrosis factor nerve growth factor receptor family inhibits T cell receptor-induced apoptosis", Proc Natl Acad Sci USA 94:6216-6221.1997.
Clark et al., "2-Benzenesulfonyl-8a-Benzyl-Hexahydro-2H-Isoguinolin-6-ones as Selective Glucocorticoid Receptor Antagonists", Bioorganic & Medicinal Chemistry Letters, vol. 17, No. 20, Sep. 14, 2007, pp. 5704-5708.
Hunt et al., "Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoguinolin-4a-yl)(4-trifluoromethyl)pyridin-2-yl)methanone (CORT125134): A Selective Glucocorticoid Receptor (GR) Antagonist", Journal of Medicinal Chemistry, vol. 60, No. 8, Apr. 3, 2017, pp. 3405-3421.
Ramsay, "Immune Checkpoint Blockade Immunotherapy to Activate Anti-Tumour T-Cell Immunity", British Journal of Haematology, vol. 162 No. 3, 2013, pp. 313-325.

(Continued)

*Primary Examiner* — Alana Harris Dent
(74) *Attorney, Agent, or Firm* — Kilpatrick Townsend & Stockton LLP

(57) ABSTRACT

This invention provides a method that combines a checkpoint inhibitor and a glucocorticoid receptor modulator to treat cancer, e.g., a checkpoint inhibitor sensitive cancer.

13 Claims, 3 Drawing Sheets

(56) References Cited

OTHER PUBLICATIONS

Skor et al., "Glucocorticoid Receptor Antagonism as a Novel Therapy for Triple-Negative Breast Cancer", Clinical Cancer Research, vol. 19, No. 22, Sep. 9, 2013, pp. 6163-6173.
EP17760608.4, "Extended European Search Report", dated Oct. 9, 2019, 10 pages.
JP2018-545599, "Office Action", dated Oct. 16, 2019, 10 pages.
SG11201807421T, "Written Opinion", dated Sep. 26, 2019, 7 pages.
Hinrichs et al., "Glucocorticoids Do Not Inhibit Antitumor Activity of Activated CD8+ T Cells," J Immunother. (2005) 28(6):517-524.
Schlossmacher et al., "Glucocorticoid receptor-mediated apoptosis: mechanisms of resistance in cancer cells," Journal of Endocrinology (2011) 211:17-25.
PCT/US2017/019948, International Search Report and Written Opinion, dated May 25, 2017, 8 pages.
Application No. IDPID201807524, Office Action, dated Dec. 16, 2020, 4 pages.
Application No. SG11201807421T, Further Written Opinion, dated Jan. 20, 2021, 7 pages.

* cited by examiner

USE OF GLUCOCORTICOID RECEPTOR MODULATORS TO POTENTIATE CHECKPOINT INHIBITORS

CROSS-REFERENCE TO RELATED APPLICATIONS

This application is a U.S. National Phase under 35 U.S.C. § 371 of PCT Application No. PCT/US2017/019948, filed Feb. 28, 2017, which claims the benefit of, and priority to, U.S. Provisional Patent Application Ser. No. 62/302,106 filed Mar. 1, 2016, and claims the benefit of, and priority to, U.S. Provisional Patent Application Ser. No. 62/320,276 filed Apr. 8, 2016. The content of each of the aforementioned applications is herein incorporated by reference in its entirety.

BACKGROUND

Cancer is a group of varied diseases characterized by uncontrolled growth and spread of abnormal cells. The pathways regulating cell division and or cellular communication become altered in cancer cells such that the effects of these regulatory mechanisms in controlling and limiting cell growth fails or is bypassed. Through successive rounds of mutation and natural selection, a group of abnormal cells, generally originating from a single mutant cell, accumulates additional mutations that provide selective growth advantage over other cells, and thus evolves into a cell type that predominates in the cell mass. As the cancer cells further evolve, some become locally invasive and then metastasize to colonize tissues other than the cancer cell's tissue of origin. This property along with the heterogeneity of the tumor cell population makes cancer a particularly difficult disease to treat and eradicate.

Traditional cancer therapies take advantage of the higher proliferative capacity of cancer cells and their increased sensitivity to DNA damage: Ionizing radiation, including γ-rays and x-rays, and cytotoxic agents, such as bleomycin, vinblastine, cyclophosphamide, 5'-fluorouracil, and methotrexate rely upon a generalized damage to DNA and destabilization of chromosomal structure which eventually leads to destruction of cancer cells. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues, and compromise the long-term health of the patient.

Recently, immunotherapy targeting immune checkpoint signaling pathways has been shown to be effective in treating cancer. These pathways suppress immune response and are crucial for maintaining self-tolerance, modulating the duration and amplitude of physiological immune responses in peripheral tissues, and minimizing collateral tissue damage. It is believed that tumor cells can activate the immune checkpoint signaling pathways to decrease the effectiveness of the immune response against tumor tissues. Many of these immune checkpoint signaling pathways are initiated by interactions between checkpoint proteins present on the surface of the cells participating in the immune responses, e.g., T cells, and their ligands, thus they can be readily blocked by agents or modulated by recombinant forms of the checkpoint proteins or ligands or receptors. The agents blocking the immunosuppression pathway induced by checkpoint proteins are commonly referred to as checkpoint inhibitors and a few have been commercialized. Cytotoxic T-lymphocyte-associated antigen 4 (CTLA4) antibodies, blocking the immunosuppression pathway by the checkpoint protein CTLA4, were the first of this class of immunotherapeutics to achieve US Food and Drug Administration (FDA) approval. Clinical findings with blockers of additional immune-checkpoint proteins, such as programmed cell death protein 1 (PD-1), indicate broad and diverse opportunities to enhance anti-tumor immunity with the potential to produce durable clinical responses.

Glucocorticoid receptor (GR) mediated signaling pathways have dynamic biologic effects involving different components of the immune system and their in vivo effects are unpredictable. For example, glucocorticoids have been reported to have both immunosuppressive effects such as, suppression of proflammatory cytokines, promotion of anti-inflammatory cytokines, inhibition of dendritic cells, suppression of natural killer cells, promotion of T-regulatory cells, and induction of T cell apoptosis,—and immune-enhancing effects, See Hinrichs J. Immunother. 2005: 28 (6): 517-524. The effects of GR mediated signaling pathway on cancer cells is likewise elusive. On one hand, it is believed that activating the GR signaling pathways induce apoptosis in certain types of cancer cells, for example, malignant lymphoid cancers. See Schlossmacher, *J. Endocrino.* (2011). On the other hand, it has also been reported that agents blocking the GR signaling pathway can potentiate chemotherapy in killing cancer cells. See U.S. Pat. No. 9,149,485. This current invention uses a novel combination therapy that targets both the checkpoint signaling pathway and GR signaling pathway to treat patients suffering from a tumor load.

SUMMARY

The cancer treatment method disclosed herein includes administering to a patient suffering from a tumor load a therapeutic amount of a checkpoint inhibitor and a selective glucocorticoid receptor modulator (SGRM) in an amount effective to potentiate the activity of the checkpoint inhibitor. The combination therapy of the checkpoint inhibitor and SGRM provides superior tumor load reduction compared to treatment with a checkpoint inhibitor alone.

In some cases, the checkpoint inhibitor is an antibody against at least one checkpoint protein, e.g., PD-1, CTLA-4, PD-L1 or PD-L2. In some cases, the checkpoint inhibitor is an antibody that is effective against two or more of the checkpoint proteins selected from the group of PD-1, CTLA-4, PD-L1 and PD-L2.

In some cases, the checkpoint inhibitor is a small molecule, non-protein compound that inhibits at least one checkpoint protein. In one embodiment, the checkpoint inhibitor is a small molecule, non-protein compound that inhibits a checkpoint protein selected from the group consisting of PD-1, CTLA-4, PD-L1 and PD-L2.

In one embodiment, the SGRM is mifepristone. In some cases, the SGRM is a compound having a non-steroidal backbone. In some cases, the SGRM is a fused azadecalin.

In some cases, the SGRM is CORT 125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

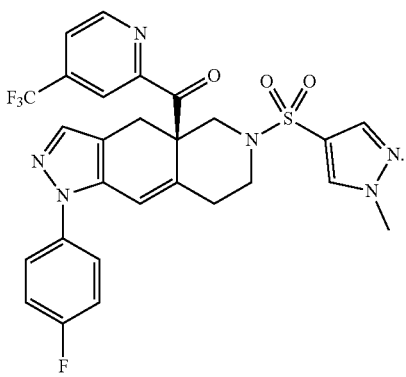 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

In some cases, the SGRM is mifepristone.

In some cases, the SGRM is CORT125281, i.e., ((4aR, 8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the following structure:

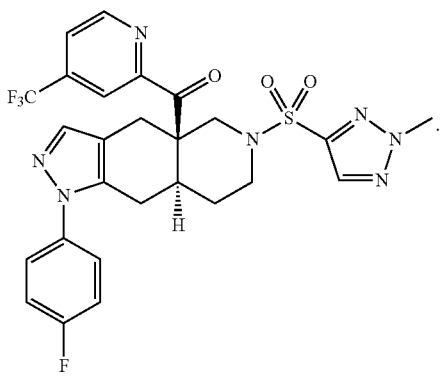 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

In one embodiment, the cancer expresses the glucocorticoid receptor (GR+).

In some cases, the cancer is a GR+ cancer and the cancer is selected from the group consisting of breast cancer, prostate cancer, melanoma, sarcoma, renal cell cancer, head and neck cancer, hepatocellular cancer, glioblastoma, cervical cancer, neuroendocrine cancer, bladder cancer, prostate cancer, esophageal cancer, mesothelioma, lung cancer, ovarian cancer, pancreatic cancer, gall bladder cancer, gastric cancer, endometrial cancer, and colon cancer.

In one embodiment, the checkpoint inhibitor and SGRM are co-administered. In a preferred embodiment, the SGRM is CORT125134 and the checkpoint inhibitor is an antibody against PD-1.

In some embodiments, provided herein is a SGRM for use in combination with a checkpoint inhibitor in a method of treating a patient hosting a tumor load, the method comprising administering to a patient suffering from a tumor load a therapeutic amount of a checkpoint inhibitor and a selective glucocorticoid receptor modulator (SGRM) in an amount effective to potentiate the activity of the checkpoint inhibitor. In addition, all the related embodiments described above are also included in these embodiments of the disclosure.

DETAILED DESCRIPTION

A. Introduction

Figure 1:
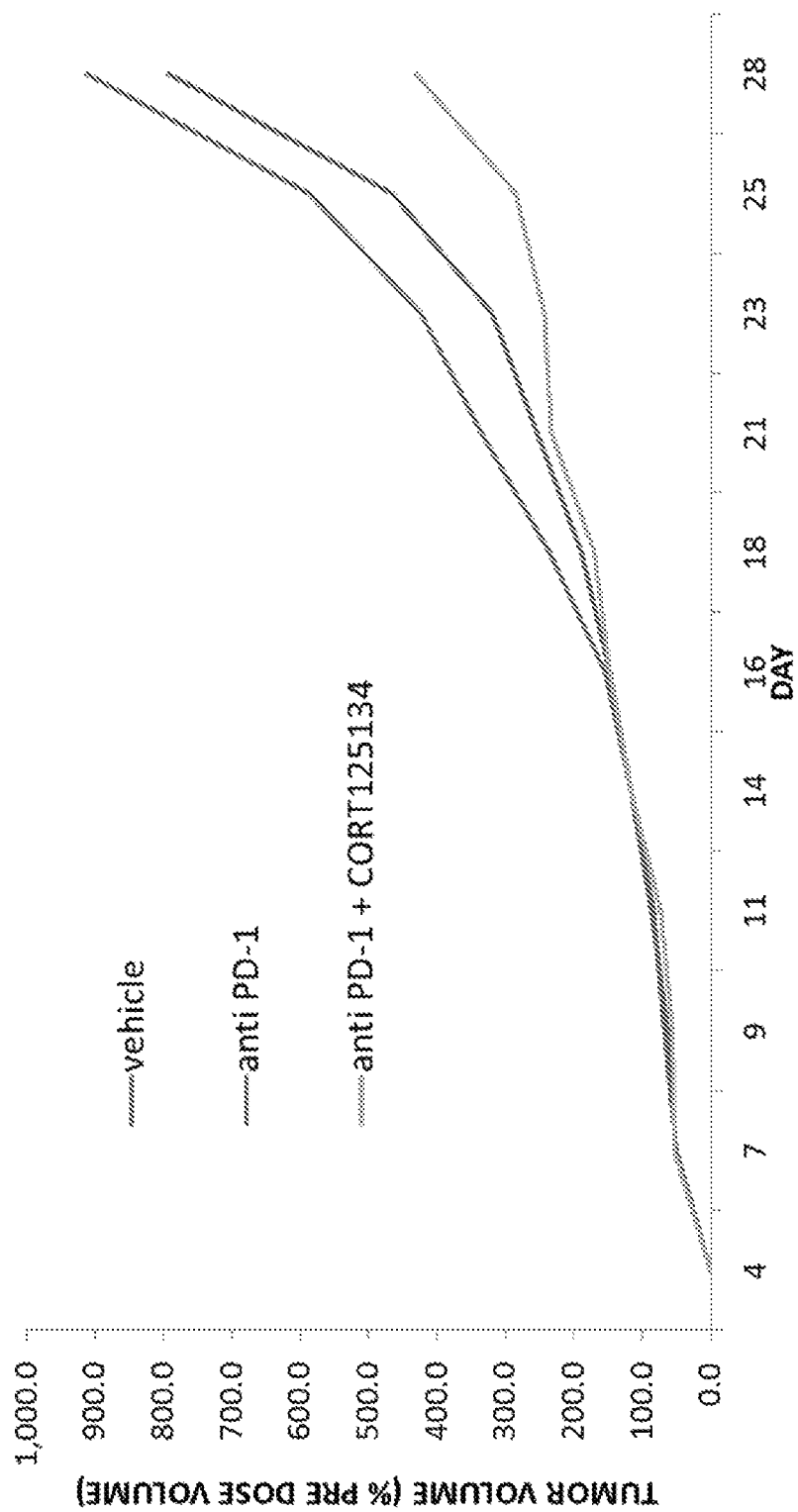
FIG. 1 shows the tumor growth data from three (3) groups of mice that were treated with 1) anti-PD-1 vehicle (PBS, 10 ml/kg), i. p. twice a week and the CORT125134 vehicle p.o. (10% DMSO, 0.1% Tween 80 and 89.9% HPMC (0.5%), 10 ml/kg) daily; 2) the mouse anti PD-1 antibody (clone RPM1-14, 10 mg/kg) i. p. twice a week; and 3) the mouse anti PD-1 antibody (clone RPM1-14, 10 mg/kg) i. p. twice a week and CORT125134 (a SGRM) (30 mg/kg) orally on a daily basis, respectively. The result shows that the combination of anti PD-1 and CORT125134 is superior to both the anti PD-1 group and the vehicle group in reducing tumor growth.

This method disclosed herein can be used to treat a patient hosting a tumor load by administering at least one SGRM and at least one checkpoint inhibitor. The checkpoint inhibitor is administered in an amount that is effective to treat the cancer when administered alone or in combination with a SGRM. The SGRM is administered in an amount that is effective to potentiate the checkpoint inhibitor's activity of blocking the checkpoint signaling pathways. In some cases, the tumor load is caused by a checkpoint inhibitor sensitive cancer.

B. Definitions

As used herein, the term "subject" or "patient" refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. In some cases, a subject may suffer from one or more types of cancer simultaneously, at least one of which is targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer, sarcoma, breast cancer, hepatocellular tumor, glioblastoma, neuroendocrine tumor, bladder cancer, gall bladder cancer, gastric cancer, endometrial cancer, and mesothelioma.

As used herein, the term "tumor load" or "tumor burden" generally refers to the number of cancer cells, the size of a tumor, or the amount of cancer in the body in a subject at any given time. Tumor load can be detected by e.g., measuring the expression of tumor specific genetic markers and measuring tumor size by a number of well-known, biochemical or imaging methods disclosed herein, infra.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

As used herein, the term "checkpoint inhibitor sensitive cancer" refers to a cancer that is responsive to checkpoint inhibitors. Administration of one or more checkpoint inhibitors to patients having such a tumor would cause a reduction in the tumor load or other desired beneficial clinical outcome related to cancer improvement.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to invoke an antitumor response. The effective amount can be an amount effective to evoke a humoral and/or cellular immune response in the recipient subject leading to growth inhibition or death of target cells. For the purpose of this disclosure, the therapeutic amount of the checkpoint inhibitor is an amount that would reduce tumor load or bring about other desired beneficial clinical outcomes related to cancer improvement.

As used herein, the phrase "an amount effective to potentiate" refers to the amount of of a pharmacological agent effective to enhance the activity of another therapeutic agent in treating, eliminating, or mitigating at least one symptom of the disease being treated. The agent used to potentiate the activity of another can be effective or non-effective in treating, eliminating, or mitigating the symptom of the disease itself. In some cases, the potentiating agent is not effective, and the effect of potentiation can be shown by the increased degree in relieving the symptom resulting from treatment by the combination of the two agents as compared to the treatment with the therapeutic agent alone. In some cases, the potentiating agent itself is effective in treating the symptoms, and the potentiating effect can be shown by a synergistic effect between the potentiating agent and the therapeutic agent. For the purpose of this disclosure, the SGRM acts as a potentiating agent to potentiate the activity of checkpoint inhibitors in treating cancer, regardless whether the SGRM would be effective in treating the cancer if administered alone. In some embodiments, a potentiating effect of 10% to 1000% can be achieved. In some embodiments, the SGRM is administered at an amount that renders the tumor sensitive to the checkpoint inhibitor, i.e., a showing of a reduction of tumor load or other related clinical benefit that would not otherwise appear when the tumor is treated with the checkpoint inhibitor in the absence of the SGRM.

As used herein, the term "combination therapy" refers to the administration of at least two pharmaceutical agents to a subject to treat a disease. The two agents may be administered simultaneously, or sequentially in any order during the entire or portions of the treatment period. The two agents may be administered following the same or different dosing regimens. In some cases, one agent is administered following a scheduled regimen while the other agent is administered intermittently. In some cases, both agents are administered intermittently. In some embodiments, the one pharmaceutical agent, e.g., a SGRM, is administered every day, and the other pharmaceutical agent, e.g., a checkpoint inhibitor, is administered weekly or biweekly.

As used herein, the terms "administer," "administering," "administered" or "administration" refer to providing a compound or a composition (e.g., one described herein), to a subject or patient.

As used herein, the term "co-administer" refers to administer two compositions simultaneously or within a short time of each other, e.g., within about within 0.5, 1, 2, 4, 6, 8, 10, 12, 16, 20, or 24 hours of each other.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless whether it exists in a free form or an associated form.

As used herein, the term "small molecule, non-protein compound" refers to a low molecular weight organic compound, which typically has a molecular weight of less than 900 daltons As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "checkpoint protein" refers to a protein that is present on the surface of certain types of cells, e.g. T cells and certain tumor cells, and can induce checkpoint signaling pathways and result in suppression of immune responses. Commonly known checkpoint proteins include CTLA4, PD-1, PD-L1, LAG3, B7-H3, B7-H4, CD160, CD244, VISTA, TIGIT, and BMA. (Pardol, 2012, Nature Reviews Cancer 12:252-264; Baksh, 2015, Semin Oncol. 2015 June; 42(3):363-77). Among these, CTLA4, PD-1 and PD-L1 are most well studied and therapies targeting these proteins are more clinically advanced than therapies targeting other checkpoint proteins.

As used herein, the term "PD-1" refers to Programmed Cell Death Protein 1 (also known as CD279), a cell surface membrane protein of the immunoglobulin superfamily. PD-1 is expressed by B cells, T cells and NK cells. The major role of PD-1 is to limit the activity of T cells in peripheral tissues during inflammation in response to infection, as well as to limit autoimmunity. PD-1 expression is induced on activated T cells and binding of PD-1 to one of its endogenous ligands acts to inhibit T cell activation by inhibiting stimulatory kinases. PD-1 also acts to inhibit the TCR "stop signal". PD-1 is highly expressed on Treg cells (regulatory T cells) and may increase their proliferation in the presence of ligand (Pardoll, 2012, Nature Reviews Cancer 12:252-264).

As used herein, the term "PD-L1" refers to Programmed Cell Death 1 ligand 1 (also known as CD274 and B7-H1), a ligand for PD-1. PD-L1 is found on activated T cells, B cells, myeloid cells, macrophages, and tumor cells. Although there are two endogenous ligands for PD-1, PD-L1 and PD-L2, anti-tumor therapies have focused on anti-PD-L1. The complex of PD-1 and PD-L1 inhibits proliferation of CD8+ T cells and reduces the immune response (Topalian et al., 2012, N. Engl J. Med. 366:2443-54; Brahmer et al., 2012, N. Engl J. Med. 366:2455-65).

As used herein, the term "CTLA4" refers to Cytotoxic T-lymphocyte antigen 4 (also known as CD152), a member of the immunoglobulin superfamily that is expressed exclusively on T cells. CTLA4 acts to inhibit T cell activation and is reported to inhibit helper T cell activity and enhance regulatory T cell immunosuppressive activity. Although the precise mechanism of action of CTL4-A remains under investigation, it has been suggested that it inhibits T cell activation by outcompeting CD28 in binding to CD80 and CD86 on antigen presenting cells, as well as actively delivering inhibitor signals to the T cell (Pardon, 2012; Nature Reviews Cancer 12:252-264).

As used herein, the term "checkpoint inhibitor" refers to any molecules, including antibodies and small molecules, that block the immunosuppression pathway induced by one or more checkpoint proteins.

As used herein, the term "antibody" as used herein also includes a full-length antibody as well as an "antigen-binding portion" of an antibody. The term "antigen-binding portion", as used herein, refers to one or more fragments of an antibody that retain the ability to specifically bind to an antigen (e.g., PD-1). Examples of binding fragments encompassed within the term "antigen-binding portion" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Ed fragment consisting of the VH and CH1 domains; (iv) a Fv fragment consisting of the VL and VH domains of a single arm of an antibody, (v) a dAb fragment (Ward et al, (1989) Nature 341:544-546), which consists of a VH domain; and (vi) an isolated complementarity determining region (CDR). Furthermore, although the two domains of the Fv fragment, VL, and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and VI can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Antibodies may be polyclonal or monoclonal; xenogeneic, allogeneic, or syngeneic; or modified forms thereof, e.g. humanized, chimeric, etc. Antibodies of the invention bind specifically or substantially specifically to one or more checkpoint proteins. The term "monoclonal antibodies" refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition typically displays a single binding affinity for a particular antigen with which it immunoreacts.

As used herein, the term "antibody effective against a checkpoint protein" refers to an antibody that can bind to the checkpoint protein and antagonize the checkpoint protein's function in suppressing immune response. For example, an antibody against PD-1 refers to an antibody that can bind to PD-1 and block the PD-1's inhibitory function on the immune response, through e.g., blocking the interactions between PD-1 and PD-L1. In some cases, an antibody can be against two checkpoint proteins, i.e., having the ability of binding to two checkpoint proteins and inhibiting their function.

As used herein, the term "Glucocorticoid receptor" ("GR") refers to a family of intracellular receptors which specifically bind to cortisol and/or cortisol analogs. The glucocorticoid receptor is also referred to as the cortisol receptor. The term includes isoforms of GR, recombinant GR and mutated GR. "Glucocorticoid receptor" ("GR") refers to the type II GR which specifically binds to cortisol and/or cortisol analogs such as dexamethasone (See, e.g., Turner & Muller, J Mol Endocrinol Oct. 1, 2005 35 283-292).

"Glucocorticoid receptor modulator" ("GRM") also known and described in the scientific and patent literature as a glucocorticoid receptor antagonist refers to any compound which inhibits any biological response associated with the binding of GR to an agonist. For example, a GR agonist, such as dexamethasone, increases the activity of tyrosine aminotransferase (TAT) in HepG2 cells (a human liver hepatocellular carcinoma cell line; ECACC, UK). Accordingly, GR modulators of the present invention can be identified by measuring the ability of the compound to inhibit the effect of dexamethasone. TAT activity can be measured as outlined in the literature by A. Ali et al., J. Med. Chem., 2004, 47, 2441-2452. A modulator is a compound with an $IC_{50}$ (half maximal inhibition concentration) of less than 10 micromolar. See Example 1, infra.

As used herein, the term "selective glucocorticoid receptor modulator" refers to any composition or compound which inhibits any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor antagonist bind GR with an affinity that is 10× greater ($^{1}/_{10}{}^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor antagonist binds GR with an affinity that is 100× greater ($^{1}/_{100}{}^{th}$ the $K_d$ value) than its affinity to the MR, AR, or PR, both the MR and PR, both the MR and AR, both the AR and PR, or to the MR, AR, and PR. In another embodiment, the selective glucocorticoid receptor antagonist binds GR with an affinity that is 1000× greater ($^{1}/_{1000}{}^{th}$ the $K_d$ value) than its affinity to the MR, AR, or PR, both the MR and PR, both the MR and AR, both the AR and PR, or to the MR, AR, and PR.

As used herein, the term "composition" is intended to encompass a product comprising the specified ingredients such as the said compounds, their tautomeric forms, their derivatives, their analogues, their stereoisomers, their polymorphs, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

As used herein, the phrase "not otherwise indicated for treatment with a glucocorticoid receptor modulator" refers to refers to a patient that is not suffering from any condition recognized by the medical community to be effectively treatable with glucocorticoid receptor antagonists, with the exception of hepatic steatosis. Conditions known in the art and accepted by the medical community to be effectively treatable with glucocorticoid receptor antagonists include: psychosis associated with interferon-α therapy, psychotic major depression, dementia, stress disorders, autoimmune disease, neural injuries, and Cushing's syndrome, In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I

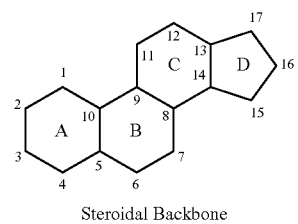

Steroidal Backbone

The two most commonly known classes of structural modifications of the cortisol steroid backbone to create glucocorticoid antagonists include modifications of the 11-β hydroxy group and modification of the 17-β side chain (See, e.g., Lefebvre (1989) J. Steroid Biochem. 33: 557-563).

As used herein, the phrase "non-steroidal backbone" in the context of SGRMs refers to SGRMs that do not share structural homology to, or are not modifications of, cortisol with its steroid backbone containing seventeen carbon atoms, bonded in four fused rings. Such compounds include synthetic mimetics and analogs of proteins, including partially peptidic, pseudopeptidic and non-peptidic molecular entities.

Non-steroidal SGRM compounds include SGRMs having a fused azadecalin backbone, a heteroaryl ketone fused azadecalin backbone, and an octahydro fused azadecalin backbone. Exemplary glucocorticoid receptor modulators having a fused azadecalin backbone include those described in U.S. Pat. Nos. 7,928,237 and 8,461,172. Exemplary glucocorticoid receptor modulators having a heteroaryl ketone fused azadecalin backbone include those described in U.S. 2014/0038926, Exemplary glucocorticoid receptor modulators having an octahydro fused azadecalin backbone include those described in U.S. Provisional Patent Appl. No. 61/908,333, entitled Octahydro Fused Azadecalin Glucocorticoid Receptor Modulators, filed on Nov. 25, 2013.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec butyl, tert butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, —$C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornene, [2.2.2] bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —S(O)$^2$. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline;

quinazoline includes 2- and 4-quinoazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in the present invention.

As used herein, the term "$GR^+$ cancer" refers to a cancer that expresses GR. GR expression can be determined by routine molecular and biochemical methods in the art, for example, immunohistochemistry staining. In one embodiment, a $GR^+$ cancer is one that has at least 10% tumor cells showing nuclear staining of GR at any intensity. In another embodiment, a $GR^+$ cancer is one that has a H-score, using methods disclosed in section "identifying GR expression", equal or greater than a predetermined threshold, e.g., 150.

C. Select Patient Population i. Diagnosing Cancer

Cancers are characterized by uncontrolled growth and/or spread of abnormal cells. A biopsy is tyically taken and the cell or tissue from the biopsy is examined under a microscope in order to confirm a suspected condition. In some cases, additional tests need to be performed on the cells' proteins, DNA, and RNA to verify the diagnosis.

ii. Identifying Checkpoint Inhibitor Sensitive Cancer

In some embodiments of the invention, methods are used to treat patients having at least one checkpoint inhibitor sensitive cancer. Checkpoint inhibitor sensitive cancers are those that are responsive to checkpoint inhibitors, i.e., administration of one or more checkpoint inhibitors can reduce tumor load or achieve beneficial or desired clinical results related to cancer improvement. For example, the administration of the checkpoint inhibitor may bring about one or more of the following: reducing the number of cancer cells; reducing the tumor size; inhibiting (i.e., slowing to some extent and/or stop) cancer cell infiltration into peripheral organs; inhibiting (i.e., slowing to some extent and/or stop) tumor metastasis; inhibiting, to some extent, tumor growth; and/or relieving to some extent one or more of the symptoms associated with the disorder; shrinking the size of the tumor; decreasing symptoms resulting from the disease; increasing the quality of life of those suffering from the disease; decreasing the dose of other medications required to treat the disease; delaying the progression of the disease; and/or prolonging survival of patients.

Checkpoint inhibitor sensitive tumors often have high expression of ligands, e.g., PD-L1 or B7, that bind to checkpoint proteins, PD-1 or CTLA-4, respectively. These interactions suppress immune responses against the tumor cells. Non-limiting examples of checkpoint inhibitor sensitive tumors include lung cancer, liver cancer, ovarian cancer, cervical cancer, skin cancer, bladder cancer, colon cancer, breast cancer, glioma, renal carcinoma, stomach cancer, esophageal cancer, oral squamous cell cancer, head/neck cancer, melanoma, sarcoma, renal cell tumor, hepatocellular tumor, glioblastoma, neuroendocrine tumor, bladder cancer, pancreatic cancer, gall bladder cancer, gastric cancer, prostate cancer, endometrial cancer, thyroid cancer and mesothelioma.

iii. Identifying GR Expression

In some embodiments, the checkpoint inhibitor sensitive cancer is also a GR+ cancer. GR expression in cancer cells can be examined by using one or more of the routine biochemical analyses. In some embodiments, GR expression is determined by detecting GR transcript expression, using methods such as microarray and RT-PCR. In other embodiments, GR expression is determined by detecting protein expression, using methods such as, western blot analysis and immunohistochemistry staining. In yet other embodiments, the GR expression is determined using a combination of these methods.

In a preferred embodiment, immunohistochemistry staining is performed and a H-score method is used to quantify the expression of GR on cancer tissues. In one exemplar assay, Formalin-fixed, paraffin-embedded tumor tissue sections are deparaffinized and treated with antigen retrieval solution to render the glucocorticoid receptors readily accessible to anti-GR antibodies. Anti-GR antibodies are then incubated with the tissue sections and the antibodies bound to the GR on the tissue sections are detected by addition of a horse peroxidase (HRP) conjugated secondary antibody that recognizes the anti-GR antibody. The HRP on the secondary antibody conjugate catalyzes a colorimetric reaction and upon contacting the appropriate substrate, produces a staining in the locations where GR is present. In one approach, the intensity level of the GR staining is represented by 0 for negative staining. 1+ for weak staining, 2+ for moderate staining, and 3+ for strong staining. See www.ihcworld.com/ihc_scoring.htm. The percentage of GR+ cells of each intensity level is multiplied with the intensity level, and the results for all intensity levels are summed to generate a H-score between 0-300. In one embodiment, the cancer type having a H-score equal to or higher than a predetermined threshold is considered GR+ cancer. In a preferred embodiment, the threshold is 150. In another embodiment, a GR+ cancer is one that has at least 10% tumor cells showing GR staining at any intensity. A number of cancer types are GR+, using the threshold of H-score 150. See Table 1, below. A majority of these cancer types are also checkpoint inhibitor sensitive cancers as shown by published results of clinical trials. See, www.clinicaltrial.gov.

D. Checkpoint Inhibitors

The method disclosed herein uses at least one SGRM in combination with at least one checkpoint inhibitor to treat cancers. In some embodiments, the checkpoint inhibitor is an antibody ("CIA") against at least one checkpoint protein. In some embodiments, the checkpoint inhibitor is a small molecule, non-protein compound ("CIC") that blocks the immunosuppression pathway induced by one or more checkpoint proteins.

i. Checkpoint Inhibitor Antibodies ("CIA")

In one embodiment, the method for treating cancer comprises administering a SGRM in combination with a checkpoint inhibitor antibody. Such an antibody can block the immunosuppression activity of the checkpoint protein. A number of such antibodies have already been shown to be effective in treating cancers, e.g., antibodies against PD-1, CTLA4, and PD-L1.

Anti-PD 1 antibodies have been used for the treatment of melanoma, non-small-cell lung cancer, bladder cancer, prostate cancer, colorectal cancer, head and neck cancer, triple-negative breast cancer, leukemia, lymphoma and renal cell cancer. Exemplary anti-PD-1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.).

Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies. Exemplary anti-PD-L1 antibodies include MDX-1105 (MEDAREX), MEDI4736 (MEDIMMUNE), MPDL3280A (GENENTECH) and BMS-936559 (BRISTOL-MYERS SQUIBB).

Anti-CTLA4 antibodies have been used in clinical trials for the treatment of melanoma, prostate cancer, small cell lung cancer, non-small cell lung cancer. A significant feature of anti-CTL4A is the kinetics of anti-tumor effect, with a lag period of up to 6 months after initial treatment required for physiologic response. In some cases, tumors may actually increase in size after treatment initiation, before a reduction is seen (Pardoll, 2012, Nature Reviews Cancer 12:252-264). Exemplary anti-CTLA4 CIAs include ipilimumab (Bristol-Myers Squibb) and tremelimumab (PFIZER).

CIAs against other checkpoint proteins, such as LAG3, B7-H3, B7-H4 and TIM3, may also be used in combination with the SGRMs disclosed herein to treat cancers.

The CIAs used in this disclosure can be a combination of different CIAs, especially if the target checkpoint proteins, e.g., PD-1 and CTLA4, suppress immune response via different signaling pathways. Thus a combination of CIAs against either of the checkpoint proteins or a single CIA that is against both checkpoint proteins may provide an enhanced immune response.

Generating CIAs

CIAs can be developed using methods well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Monoclonal antibodies can be obtained by injecting mice with a composition comprising an antigen, e.g. a checkpoint protein or an epitope of thereof, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Monoclonal antibodies produced can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 27.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to a checkpoint protein, the antibodies can be sequenced and subsequently prepared by recombinant techniques. Humanization and chimerization of murine antibodies and antibody fragments are well known to those skilled in the art. See, for example, Leung et al. Hybridoma 13:469 (1994); US20140099254 A1.

Human antibodies can be produced using transgenic mice that have been genetically engineered to produce specific human antibodies in response to antigenic challenge using a checkpoint protein. See Green et al., *Nature Genet.* 7: 13 (1994), Lonberg et al., *Nature* 368:856 (1994). Human antibodies against a checkpoint protein also can be constructed by genetic or chromosomal tranfection methods, phage display technology, or by in vitro activated B cells. See e.g., McCafferty et al., 1990, Nature 348: 552-553; U.S. Pat. Nos. 5,567,610 and 5,229,275.

Modifyin CIAs

CIAs may also be produced by introducing conservative modifications relative to the existing CIAs. For example, a modifed CIA may comprise heavy and light chain variable regions, and/or a Fc region that are homologous to the counterparts of an antibody produced above. The modified CIA that can be used for the method disclosed herein must retain the desired functional properties of being able to block the checkpoint signaling pathway.

CIAs may also be produced by altering protein modification sites. For example, sites of glycosylation of the antibody can be altered to produce an antibody lacking glycosylation and the so modified CIAs typically have increased affinity of the antibody for antigen. Antibodies can also be pegylated by reacting with polyethylene glycol (PEG) under conditions in which one or more PEG groups become attached to the antibody. Pegylation can increase the biological half-life of the antibody. Antibodies having such modifications can also be used in combination with the selective GR modulator disclosed herein so long as it retains the desired functional properties of blocking the checkpoint pathways.

ii. Small Molecule, Non-Protein Checkpoint Inhibitor Compounds ("CICs")

In another embodiment, the method for treating cancer, e.g. a checkpoint inhibitor sensitive cancer, uses a SGRM in combination with a CIC. A CIC is a small molecule, non-protein compound that antagonizes a checkpoint protein's immune suppression function. Many CICs are known in the art, for example, those disclosed in PCT publications WO2015034820, WO20130144704, and WO2011082400.

CICs can also be identified using any of the numerous approaches in combinatorial library methods known in the art and disclosed in, e.g., European patent application EP2360254. The cominatorial libraries include: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

iii. Evaluating the Functional Properties of the Candidate Checkpoint Inhibitors A number of well-known assays can be used to assess whether a candidate, i.e., an antibody generated by immunizing an animal with an antigen comprising a checkpoint protein, an epitope of the checkpoint protein, or a test compound from combinatorial libraries, as disclosed above, is a checkpoint inhibitor. Non-limiting exemplar assays include binding assays—such as Enzyme-Linked Immunosorbent Assays (ELISAs), radioimmunoassays (RIA)—, Fluorescence-Activated Cell Sorting (FACS) analysis, cell-based assays, and in vivo assays.

Binding Assays

In one embodiment, the assay is a direct binding assay. The checkpoint protein can be coupled with a radioisotope or enzymatic label such that binding of the checkpoint protein and the candidate can be determined by detecting the labeled checkpoint protein in a complex. For example, a checkpoint protein can be labeled with $^{125}$I, $^{35}$S, $^{14}$C, or $^{3}$H, either directly or indirectly, and the radioisotope detected by direct counting of radio-emission or by scintillation counting. Determining the ability of candidates to bind their cognate checkpoint protein can be accomplished, e.g., by measuring direct binding. Alternatively, checkpoint protein molecules can be enzymatically labeled with, for example, horseradish peroxidase, alkaline phosphatase, or luciferase, and binding of the candidates to the target checkpoint protein is determined by conversion of an appropriate substrate to product.

Enzyme-linked immunosorbent assay (ELISA) are commonly used to evaluate a CIA candidate's binding specificity to its target checkpoint protein. In a typical assay, microtiter plates are coated with the checkpoint protein by coating overnight at 37° C. with 5 µg/ml checkpoint protein. Serum samples comprising candidate CIAs are diluted in PBS, 5% serum, 0.5% Tween-20 and are incubated in wells for 1 hour at room temperature, followed by the addition of anti-human IgG Fc and IgG F(ab')-horseradish peroxidase in the same diluent. After 1 hour at room temperature enzyme activity is assessed by addition of ABTS substrate (Sigma, St. Louis Mo.) and read after 30 minutes at 415-490 nm.

The binding kinetics (e.g., binding affinity) of the candidates also can be assessed by standard assays known in the art, such as by Biacore analysis (Biacore AB, Uppsala, Sweden). In one exemplary assay, a purified recombinant human checkpoint protein is covalently linked to a CM5 chip (carboxy methyl dextran coated chip) via primary amines, using standard amine coupling chemistry and kit provided by Biacore. Binding is measured by flowing the candidates in HBS EP buffer (provided by Biacore AB) at a concentration of 267 nM at a flow rate of 50 µl/min. The checkpoint protein-candidate association kinetics are followed for 3 minutes and the dissociation kinetics are followed for 7 minutes. The association and dissociation curves are fitted to a 1:1 Langmuir binding model using BIA evaluation software (Biacore AB). To minimize the effects of avidity in the estimation of the binding constants, only the initial segment of data corresponding to association and dissociation phases are used for fitting. The $K^D$, $K_{on}$ and $K_{off}$ values of the interaction can be measured. Preferred checkpoint inhibitors can bind to their target checkpoint protein with a Kd of $1\times10^{-7}$M or less For checkpoint proteins that block immune responses through binding to a ligand, additional binding assays may be employed to test for the ability of the candidate to block binding of the ligands to the checkpoint protein. In one exemplary assay, flow cytometry is used to test the blocking of the binding of the ligand (e.g., PD-L1) to the checkpoint protein (e.g., PD-1) expressed on transfected CHO cells. Various concentrations of the candidate are added to the suspension of cells expressing the checkpoint protein and incubated at 4° C. for 30 minutes. Unbound inhibitor is washed off and FITC-labeled ligand protein is added into the tubes and incubated at 4° C. for 30 minutes. FACS analysis is performed using a FACScan flow cytometer (Becton Dickinson. San Jose, Calif.). The mean fluorescent intensity (MFI) of staining of the cells indicates the amount of ligand that is bound to the checkpoint proteins. A reduced MFI in the sample to which the candidate is added indicates that the candidate is effective in blocking the binding of the ligand to the target checkpoint protein.

Homogenous Time-Resolved Fluorescence (HTRF) binding assay, such as described in PCT publication WO2015034820, can also be used to assay the candidate's ability to block the checkpoint protein-ligand interaction. In one embodiment, the CICs used in the method can inhibit the PD-1/PD-L1 interaction with $IC_{50}$ values of 10 pM or less, for example, from 0.01 to 10 pM, preferably, 1 pM or less, e.g., from 0.01 to 1 pM, as measured by the PD-1/PD-L1 Homogenous Time-Resolved Fluorescence (HTRF) binding assay.

Cell Based Assays

In another embodiment, the assay to evaluate whether a candidate is a checkpoint inhibitor is a cell based assay. The Mixed Lymphocyte Reaction (MLR) assay, as described in U.S. Pat. No. 8,008,449, is routinely used to measure T cell proliferation, production of IL-2 and/or IFN-γ. In one exemplary assay, human T cells are purified from PBMCs using a human $CD4^+$ T cell enrichment column (R&D systems). A candidate is added to a number of T cell cultures at different concentrations. The cells are cultured for 5 days at 37° C. and 100 μl of medium is taken from each culture for cytokine measurement. The levels of IFN-gamma and other cytokines are measured using OptEIA ELISA kits (BD Biosciences). The cells are labeled with $^3$H-thymidine, cultured for another 18 hours, and analyzed for cell proliferation. Results showing that, as compared to control, the culture containing the candidate shows increased T cell proliferation, increased production of IL-2, and/or IFN-gamma indicate the candidate is effective in blocking checkpoint protein's inhibition of T cell immune response.

In Vivo Assays

In another embodiment, the assay used to evaluate whether a candidate is a checkpoint inhibitor is a in vivo assay. In one exemplary assay, female AJ mice between 6-8 weeks of age (Harlan Laboratories) are randomized by weight into 6 groups. The mice are implanted subcutaneously in the right flank with $2 \times 10^6$ SA1/N fibrosarcoma cells dissolved in 200 μl of DMEM media on day 0. The mice are treated with PBS vehicle, or the candidate at a predetermined dosage. The animals are dosed by intraperitoneal injection with approximately 200 μl of PBS containing the candidate or vehicle on days 1, 4, 8 and 11. The mice are monitored twice weekly for tumor growth for approximately 6 weeks. Using an electronic caliper, the tumors are measured three dimensionally (height×width×length) and tumor volume is calculated. Mice are euthanized when the tumors reach tumor end point (1500 mm$^3$) or the mice show greater than 15% weight loss. A result showing that a slower tumor growth in the candidate treated group as compared to controls, or a longer mean time to reach the tumor end point volume (1500 mm$^3$) is an indication that the candidate has activity in inhibiting cancer growth.

E. Glucocorticoid Receptor Modulators (GRM)

The combination therapy for treating cancer disclosed herein also involves at least one selective glucocorticoid receptor modulator in combination with at least one checkpoint inhibitor to treat a cancer, e.g., a checkpoint inhibitor sensitive cancer. Provided herein, are classes of exemplary GRMs and specific members of such classes. However, one of skill in the art will readily recognize other related or unrelated SGRMs that can be employed in the treatment methods described herein.

1. GRMs Having a Steroidal Backbone

In some embodiments, an effective amount of a SGRM with a steroidal backbone is administered to a subject for cancer treatment. Steroidal GRMs can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create GRAs include modifications of the 11-β hydroxy group and modification of the 17-β side chain (See, e.g., Lefebvre, J. Steroid Biochem. 33:557-563, 1989).

Examples of steroidal GR antagonists include androgen-type steroidal compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and (17α)-17-hydroxy-19-(4-methylphenyl)androsta-4,9(11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 BL each of which is incorporated herein by reference. EP 0 763 541 B1 and Hoyberg et al., Int'l J. of Neuro-psychopharmacology, 5:Supp. 1, S148 (2002) disclose the compound (11β,17β)-11-(1,3-benzodioxo-5-yl)-17-hydroxy-17-(1-propynyl)estra-4,9-dien-3-one (ORG 34517), which in one embodiment, is administered in an amount effective to treat an ACTH-secreting tumor in a subject.

2. Removal or Substitution of the 11-β Hydroxy Group

Glucocorticoid antagonists with modified steroidal backbones comprising removal or substitution of the 11-β hydroxy group are administered in one embodiment of the invention. This class includes natural GRMs, including cortexolone, progesterone and testosterone derivatives, and synthetic compositions, such as mifepristone (Lefebvre, et al. supra). Preferred embodiments of the invention include all 11-β aryl steroid backbone derivatives because, in some cases, these compounds can be devoid of progesterone receptor (PR) binding activity (Agarwal, FEBS 217:221-226, 1987). In another embodiment an 11-β phenyl-aminodimethyl steroid backbone derivative, which is both an effective anti-glucocorticoid and anti-progesterone agent, is administered. These compositions can act as reversibly-binding steroid receptor antagonists. For example, when bound to a 11-β phenyl-aminodimethyl steroid, the steroid receptor can be maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-β-hydrox-11-β-(4-dimethyl-aminophenyl)17-α-(1-propynyl)estra-4,9-dien-3-one). Mifepristone has been shown to be a powerful antagonist of both the progesterone and glucocorticoid (GR) receptors. Thus, in some embodiments, the GRM administered to treat an ACTH-secreting tumor is mifepristone, or a salt, tautomer, or derivative thereof. In other embodiments, however, administration of mifepristone is specifically excluded as a GRM for treatment of an ACTH-secreting tumor.

Another 11-β phenyl-aminodimethyl steroid shown to have GR antagonist effects includes the dimethyl aminoethoxyphenyl derivative RU009 (RU39.009), 11-β-(4-dimethyl-aminoethoxyphenyl)-17-α-(propynyl-17-β-hydroxy-4,9-estradien-3-one) (see Bocquel, J. Steroid Biochem. Molec. Biol. 45:205-215, 1993). Another GR antagonist related to RU486 is RU044 (RU43.044) 17-β-hydrox-17-α-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions that are irreversible anti-glucocorticoids. Such compounds include α-keto-methanesulfonate derivatives of cortisol, including cortisol-21-mesylate (4-pregnene-11-β, 17-α, 21-triol-3, 20-dione-21-methane-sulfonate and dexamethasone-21-mesylate (16-methyl-9-α-fluoro-1,4-pregnadiene-11β, 17-α, 21-triol-3, 20-dione-21-methane-sulfonte). See Simons, J. Steroid Biochem. 24:25-32, 1986; Mercier, J. Steroid. Biochem. 25:11-20, 1986; U.S. Pat. No. 4,296,206.

3. Modification of the 17-Beta Side Chain Group

Steroidal anti-glucocorticoids which can be obtained by various structural modifications of the 17-β side chain are also used in the methods of the invention. This class includes synthetic antiglucocorticoids, such as dexamethasone-oxetanone, various 17, 21-acetonide derivatives and 17-beta-carboxamide derivatives of dexamethasone (Lefebvre, 1989, supra; Rousseau, Nature 279:158-160, 1979).

4. Other Steroid Backbone Modifications

GRMs used in the various embodiments of the invention include any steroid backbone modification which inhibits a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-β side chain substituent, and particularly the size of that substituent, can play a key role in determining the extent of a steroid's antiglucocorticoid activity. Substitutions in the A ring of the steroid backbone can also be important. For example, 17-hydroxypropenyl side chains can, in some cases, decrease antiglucoconicoid activity in comparison to 17-propynyl side chain containing compounds.

Additional glucocorticoid receptor antagonists known in the art and suitable for practice of the invention include 21-hydroxy-6,19-oxidoprogesterone (See Vicent, Mol. Pharm. 52:749-753, 1997), Org31710 (See Mizutani, J Steroid Biochem Mol Biol 42(7):695-704, 1992), RU43044, RU40555 (See Kim, J Steroid Biochem Mol Biol. 67(3):213-22, 1998), and RU28362.

5. Nonsteroidal Anti-Glucocorticoid Receptors Modulators

Provided herein, are classes of exemplary nonsteroidal glucocorticoid receptor modulator (GRM) and specific members of such classes that can be used for the method disclosed herein. However, one of skill in the art will readily recognize other related or unrelated glucocorticoid receptor modulators that can be employed in the treatment methods described herein. These include synthetic mimetics and analogs of proteins, including partially peptidic, pseudopeptidic and non-peptidic molecular entities. For example, oligomeric peptidomimetics useful in the invention include (α-β-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic &Medicinal Chem. 4:667-672, 1996).

Examples of nonsteroidal GR modulators include the GR antagonist compounds disclosed in U.S. Pat. Nos. 5,696, 127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2(R)-chloroethynyl-1,2,3,4,4α,9,10,10α(R)-octahydro-phenanthrene-2,7-diol ("CP 394531") and 4α(S)-benzyl-2(R)-prop-1-ynyl-1,2,3,4,4α,9,10,10α(R)-octahydro-phenanthrene-2,7-diol ("CP 409069"); and the compounds disclosed in PCT International Application No, WO 96/19458, which describes non-steroidal compounds which are high-affinity, highly selective antagonists for steroid receptors, such as 6-substituted-1,2-dihydro-N-protected-quinolines.

For additional compounds that can be utilized in the methods of the invention and methods of identifying and making such compounds, see U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

In some embodiments, the combination therapy for treating cancer involves a nonsteroidal GRM having a fused azadecalin backbone, a heteroaryl ketone fused azadecalin backbone, or an octahydro fused azadecalin backbone.

Exemplary GRMs having a fused azadecalin backbone include those described in U.S. Pat. Nos. 7,928,237; and 8,461,172 and are incorporated herein in their entirety. In some cases, the GRM having a fused azadecalin backbone has the following structure:

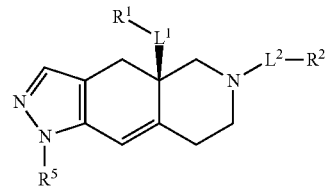

wherein

L¹ and L² are members independently selected from a bond and unsubstituted alkylene;

R¹ is a member selected from unsubstituted alkyl, unsubstituted heteroalkyl, unsubstituted heterocycloalkyl, —OR$^{1A}$, —NR$^{1C}$R$^{1D}$, —C(O)NR$^{1C}$R$^{1D}$, and —C(O)OR$^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

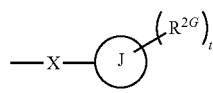

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —CF$_3$;

J is phenyl;

t is an integer from 0 to 5;

X is —S(O$_2$)—; and $R^5$ is phenyl optionally substituted with 1-5 $R^{5A}$ groups, wherein $R^{5A}$ is a member selected from hydrogen, halogen, —OR$^{5A1}$, —S(O$_2$)NR$^{5A2}$R$^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

Compounds containing fused azadecalin backbones can be prepared as described in U.S. Pat. No. 7,928,237. For example, fused azadecalin backbones can be prepared as described in Scheme 1, where, $R^5$, $R^{1A}$, $R^{1C}$, $R^{1D}$, $L^2$ and $R^2$ are as defined above in the compounds of the present invention. In Scheme 1, $L^2$-$R^2$ can be replaced by a suitable protecting group, such as BOC or benzyl, to facilitate the synthesis. Keto-ester 1 is converted directly to enone 3 by a Robinson annelation reaction involving treatment of 1 with a base (e.g. potassium or sodium alkoxides) in an alcohol solvent (e.g. methanol, ethanol, or test-butanol) followed by addition of methylvinyl ketone (MVK). The reaction is typically carried out at 0-250° C.

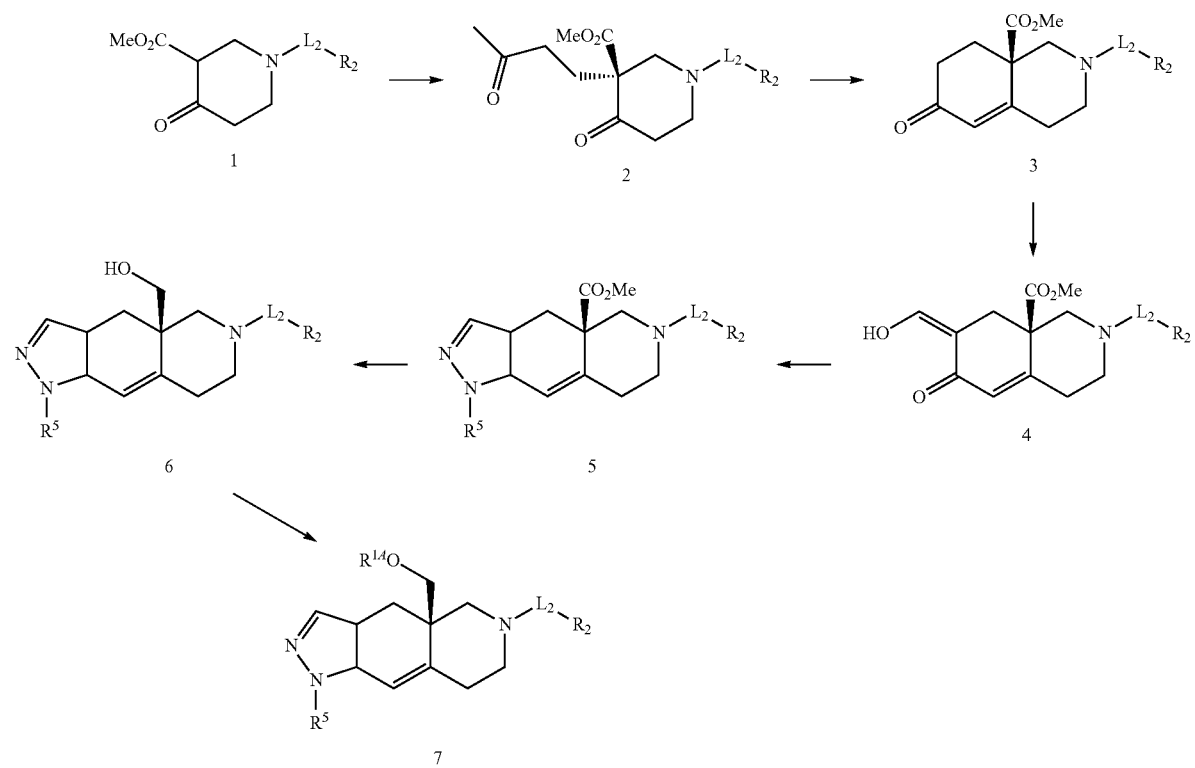

Exemplary GRMs having a heteroaryl ketone fused azadecalin backbone include those described in U.S. 2014/0038926 and is incorporated herein in its entirety. In some cases, the GRM having a heteroaryl ketone fused azadecalin backbone has the following structure:

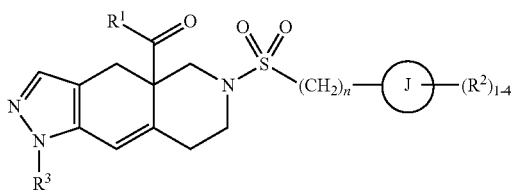

wherein
- R¹ is a heteroaryl ring having from 5 to 6 ring members and from 1 to 4 heteroatoms each independently selected from the group consisting of N, O and S, optionally substituted with 1-4 groups each independently selected from R¹ᵃ;
- each R¹ᵃ is independently selected from the group consisting of hydrogen, $C_{1-6}$ alkyl, halogen, $C_{1-6}$ haloalkyl, $C_{1-6}$ alkoxy, haloalkoxy, —CN, N-oxide, $C_{3-8}$ cycloalkyl, and $C_{3-8}$ heterocycloalkyl;
- ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
- each R² is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR²R²ᵇ, —C(O)R²ᵃ, —C(O)OR²ᵃ, —C(O)NR²ᵃR²ᵇ, —SR²ᵃ, —S(O)R²ᵃ, —S(O)₂ R²ᵃ, $C_{3-8}$ cycloalkyl, and $C_{3-8}$ heterocycloalkyl, wherein the heterocycloalkyl groups are optionally substituted with 1-4 R²ᶜ groups;
- alternatively, two R² groups linked to the same carbon are combined to form an oxo group (=O);
- alternatively, two R² groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 R²ᵈ groups;
- R²ᵃ and R²ᵇ are each independently selected from the group consisting of hydrogen and $C_{1-6}$ alkyl;
- each R²ᶜ is independently selected from the group consisting of hydrogen, halogen, hydroxy, $C_{1-6}$ alkoxy, $C_{1-6}$ haloalkoxy, —CN, and —NR²ᵃR²ᵇ;
- each R²ᵈ is independently selected from the group consisting of hydrogen and $C_{1-6}$ alkyl, or two R²ᵈ groups attached to the same ring atom are combined to form (=O),
- R³ is selected from the group consisting of phenyl and pyridyl, each optionally substituted with 1-4 R³ᵃ groups;
- each R³ᵃ is independently selected from the group consisting of hydrogen, halogen, and $C_{1-6}$ haloalkyl; and
- subscript n is an integer from 0 to 3;
- or salts and isomers thereof.

Compounds containing fused azadecalin backbones can be prepared as described in Scheme 2.

Scheme 2

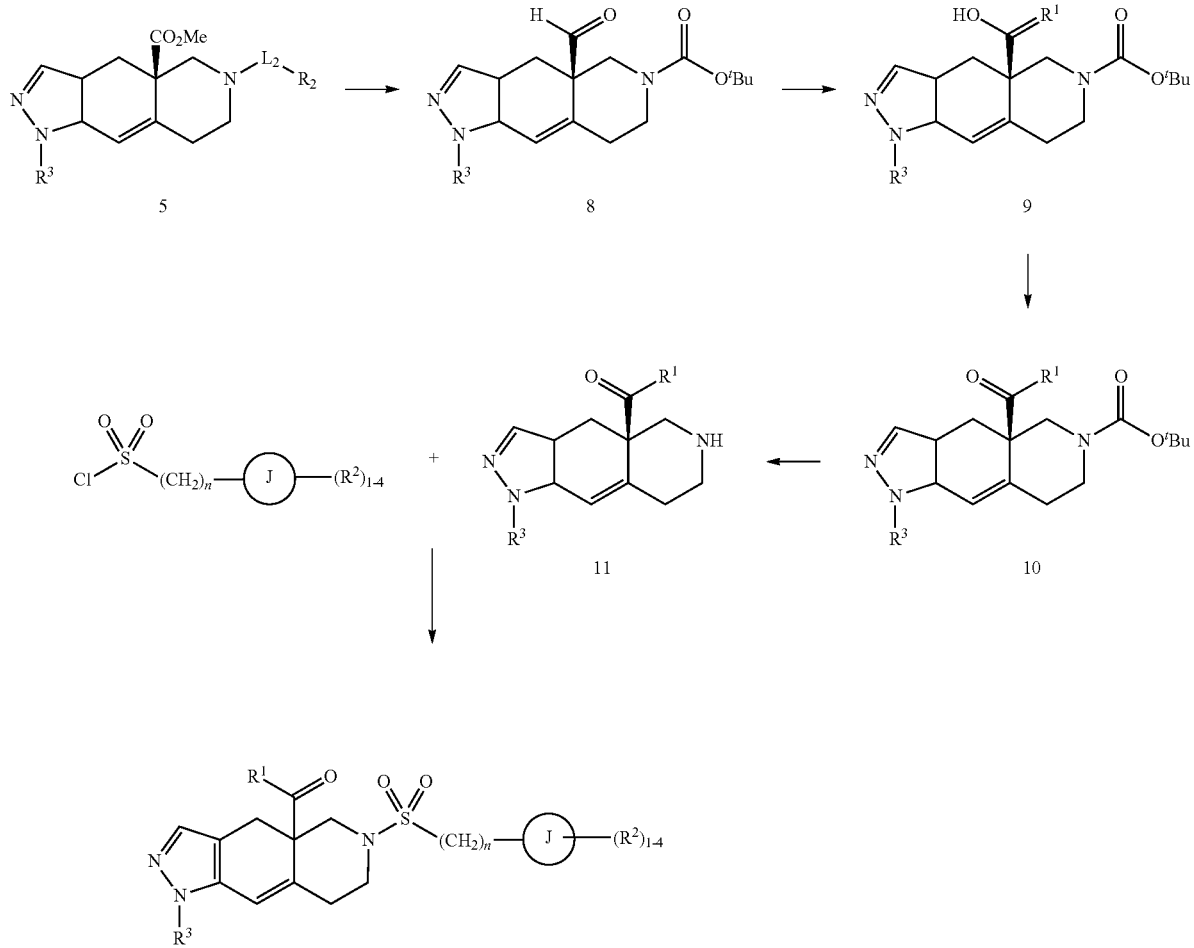

Exemplary GRMs having an octahydro fused azadecalin backbone include those described in U.S. Provisional Patent Appl. No. 61/908,333, entitled Octahydro Fused Azadecalin Glucocorticoid Receptor Modulators, filed on Nov. 25, 2013, and are incorporated herein in their entirety. In some cases, the GRM having an octahydro fused azadecalin backbone has the following structure:

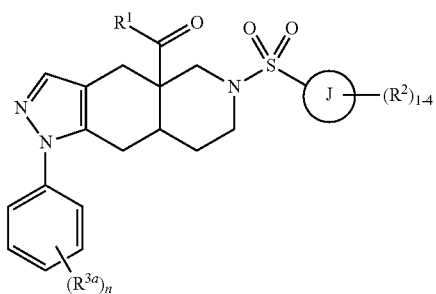

wherein
R$^1$ is a heteroaryl ring having from 5 to 6 ring members and from 1 to 4 heteroatoms each independently selected from the group consisting of N, O and S, optionally substituted with 1-4 groups each independently selected from R$^{1a}$;

each R$^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, N-oxide, and C$_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each R$^2$ is independently selected from the group consisting of hydrogen, C$_{1-6}$ alkyl, halogen, C$_{1-6}$ haloalkyl, C$_{1-6}$ alkoxy, haloalkoxy, C$_{1-6}$ alkyl-C$_{1-6}$ alkoxy, —CN, —OH, NR$^{2a}$R$^{2b}$, —C(O)R$^{2a}$, —C(O)OR$^{2a}$, —C(O)NR$^{2a}$R$^{2b}$, —SR$^{2a}$, —S(O)R$^{2a}$, —S(O)$_2$ R$^{2a}$, C$_{3-8}$ cycloalkyl, and C$_{3-8}$ heterocycloalkyl having from 1 to 3 heteroatoms each independently selected from the group consisting of N, O and S;

alternatively, two R$^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 R$^{2c}$ groups;

R$^{2a}$, R$^{2b}$ and R$^{2c}$ are each independently selected from the group consisting of hydrogen and C$_{1-6}$ alkyl;

each R$^{3a}$ is independently halogen; and subscript n is an integer from 0 to 3;

or salts and isomers thereof.

Compounds containing octahydro fused azadecalin backbones can be prepared as described in Scheme 3.

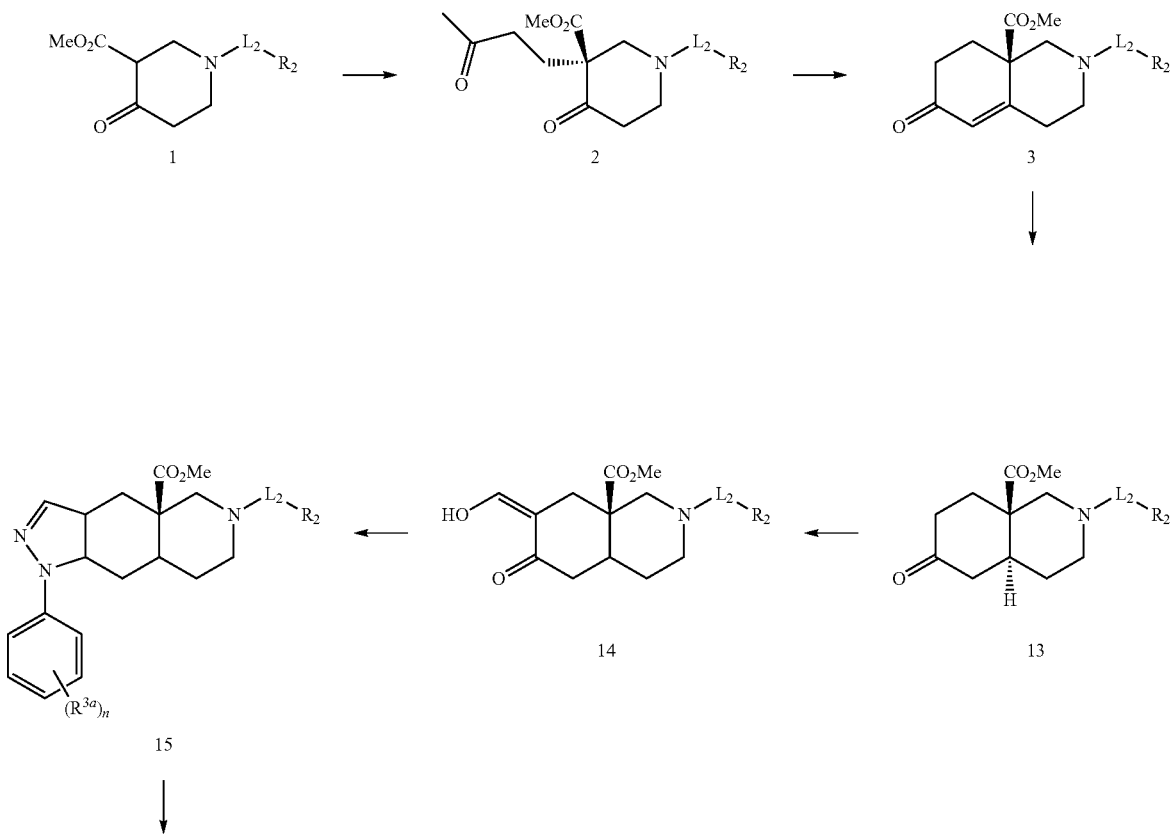

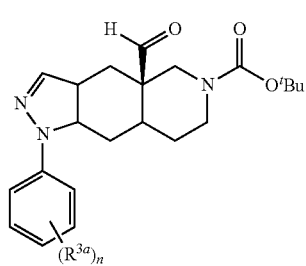

16

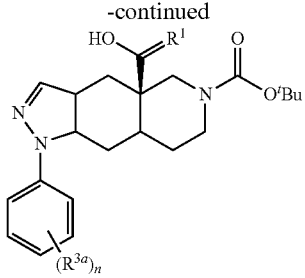

17

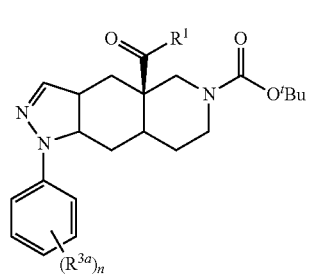

18

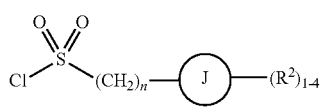

+

19

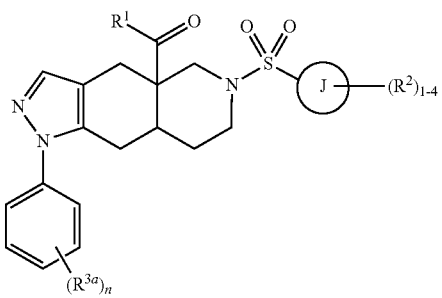

20

F. Identifying Selective Glucocorticoid Receptor Modulators (SGRMS)

To determine whether a test compound is a SGRM, the compound is first subjected to assays to measure its ability to bind to the GR and inhibit GR-mediated activities, which determines whether the compound is a glucocorticoid receptor modulator. The compound, if confirmed to be a glucocorticoid receptor modulator, is then subjected to a specificity test to determine whether the compound can bind specifically to GR as compared to non GR proteins, such as the estrogen receptor, the progesterone receptor, the androgen receptor, or the mineralocorticoid receptor. In one embodiment, a SGRM binds to GR at a substantially higher affinity, e.g., at least 10 times higher affinity, than to non-GR proteins. A SGRM may exhibit a 100 fold, 1000 fold or greater selectivity for binding to GR relative to binding to non GR proteins.

i. Binding Assays

A test compounds' ability to bind to the glucocorticoid receptor can be measured using a variety of assays, for example, by screening for the ability of the test compound to compete with a glucocorticoid receptor ligand, such as dexamethasone, for binding to the glucocorticoid receptor. Those of skill in the art will recognize that there are a number of ways to perform such competitive binding assays. In some embodiments, the glucocorticoid receptor is pre-incubated with a labeled glucocorticoid receptor ligand and then contacted with a test compound. This type of competitive binding assay may also be referred to herein as a binding displacement assay. A decrease of the quantity of labeled ligand bound to glucocorticoid receptor indicates that the test compound binds to the glucocorticoid receptor. In some cases, the labeled ligand is a fluorescently labeled compound (e.g., a fluorescently labeled steroid or steroid analog). Alternatively, the binding of a test compound to the glucocorticoid receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Bio-*

*chemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a glucocorticoid receptor ligand and the binding agent can be glucocorticoid receptor bound to a solid phase. Alternatively, the labeled analyte can be labeled glucocorticoid receptor and the binding agent can be a solid phase glucocorticoid receptor ligand. The concentration of labeled analyte bound to the capture agent is inversely proportional to the ability of a test compound to compete in the binding assay.

Alternatively, the competitive binding assay may be conducted in the liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the glucocorticoid receptor may be altered by the binding of the glucocorticoid receptor to its ligand or test compound. This alteration in the labeled glucocorticoid receptor results in a decrease or increase in the signal emitted by label, so that measurement of the label at the end of the binding assay allows for detection or quantitation of the glucocorticoid receptor in the bound state. A wide variety of labels may be used. The component may be labeled by any one of several methods. Useful radioactive labels include those incorporating $^3$H, $^{125}$I, $^{35}$S, $^{14}$C, or $^{32}$P. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art. In some cases, a test compound is contacted with a GR in the presence of a fluorescently labeled ligand (e.g., a steroid or steroid analog) with a known affinity for the GR, and the quantity of bound and free labeled ligand is estimated by measuring the fluorescence polarization of the labeled ligand.

ii. HepG2 Tyrosine Aminotransferase (TAT) Assay

Compounds that have demonstrated the desired binding affinity to GR are tested for their activity in inhibiting GR mediated activities. In one approach, the compounds are subject to a Tyrosine Aminotransferase Assay (TAT), which assesses the ability of a test compound to inhibit the induction of tyrosine aminotransferase activity by dexamethasone. See Example 1. GR modulators that are suitable for the method disclosed herein have an $IC_{50}$ (half maximal inhibition concentration) of less than 10 micromolar.

iii. Cell-Based Assays

Cell-based assays which involve whole cells or cell fractions containing glucocorticoid receptors can also be used to assay for a test compound's binding or modulation of activity of the glucocorticoid receptor. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some cases, fragments of the glucocorticoid receptor, as well as protein fusions, can be used for screening. When molecules that compete for binding with the glucocorticoid receptor ligands are desired, the GR fragments used are fragments capable of binding the ligands (e.g., dexamethasone). Alternatively, any fragment of GR can be used as a target to identify molecules that bind the glucocorticoid receptor. Glucocorticoid receptor fragments can include any fragment of, e.g., at least 20, 30, 40, 50 amino acids up to a protein containing all but one amino acid of glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1 beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

iv. Additional Assays

Further illustrative of the many assays which can be used to identify compositions utilized in the methods of the invention, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., J. *Steroid Biochem. Mol. Biol.* 41; 723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm, 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR modulator will oppose this effect.

v. Selectivity

The GR modulators selected above are then subject to a selectivity assay to determine whether they are SGRMs. Typically, selectivity assays include testing a compound that binds glucocorticoid receptor in vitro for the degree of binding to non-glucocorticoid receptor proteins. Selectivity assays may be performed in vitro or in cell based systems, as described above. Binding may be tested against any appropriate non-glucocorticoid receptor protein, including antibodies, receptors, enzymes, and the like. In an exemplary embodiment, the non-glucocorticoid receptor binding protein is a cell-surface receptor or nuclear receptor. In another exemplary embodiment, the non-glucocorticoid receptor protein is a steroid receptor, such as estrogen receptor, progesterone receptor, androgen receptor, or mineralocorticoid receptor.

The selectivity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either a direct binding assay or by assessing competitive binding to the purified GR or MR in the presence of a known ligand. In an exemplary assay, cells that stably express the glucocorticoid receptor or mineralocorticoid receptor (see, e.g., U.S. Pat. No. 5,606,021) at high levels are used as a source of purified receptor. The affinity of the ligand for the receptor is then directly measured. Those GR modulators that exhibit at least a 10 fold, 100-fold higher affinity, often 1000-fold, for the GR relative to the MR are then selected for use in the methods of the invention.

The selectivity assay may also include assaying the ability to inhibit GR-mediated activities, but not MR-mediated activities. One method of identifying such a selective GR modulator is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells The transfected host cells are then cultured in the presence and absence of a hormone, such as cortisol or an analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. GR modulators that exhibits at least a 100-fold, often 1000-fold or greater, activity towards the GR relative to the MR, PR, or AR are then selected for use in the methods disclosed herein.

An exemplar SGRM that can be used in the methods disclosed herein is CORT 125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

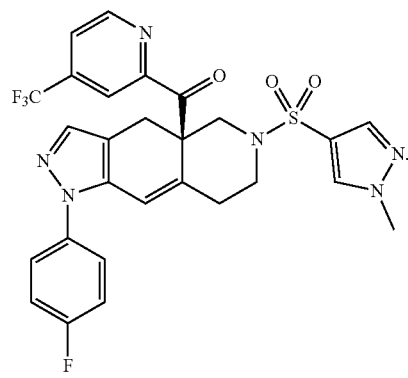 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Another exemplar SGRM that can be used in the methods disclosed herein is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-a]isoquinolin-4a-yl)(4-(trifluoromethyl)pyridin-2-yl)methanone, which has the following structure:

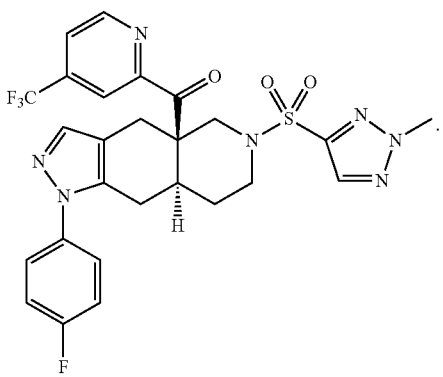 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

G. Pharmaceutical Compositions and Administration
i. Formulations

In some embodiments, the present invention provides a pharmaceutical composition including a pharmaceutically acceptable excipient and a SGRM and a pharmaceutically acceptable excipient and a CIC or a CIA.

Any of the SGRMs, CICs, or CIAs disclosed herein can be formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

The pharmaceutical compositions of the invention can be prepared and administered in a wide variety of oral, parenteral and topical dosage forms. Oral preparations, preferably for SGRMs and CICs, include tablets, pills, powder, dragees, capsules, liquids, lozenges, gels, syrups, slurries, suspensions, etc., suitable for ingestion by the patient. The pharmaceutical compositions can also be administered by injection, that is, intravenously, intramuscularly, intracutaneously, subcutaneously, intraduodenally, or intraperitoneally. Also, pharmaceutical compositions can be administered by inhalation, for example, intranasally. Additionally, non-steroidal SGRMs can be administered transdermally. Accordingly, the present invention also provides pharmaceutical compositions including a pharmaceutically acceptable carrier or excipient and a SGRM or a checkpoint inhibitor. Depending on the route of administration, the active compound can be coated in a material to protect the compound from the action of enzymes, acids and other natural conditions which may inactivate the compound.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other polar solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

For preparing pharmaceutical compositions from SGRMs or CICs, or CIAs pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution. Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that it can be delivered by a syringe without difficulties. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a checkpoint inhibitor, e.g., a CIA, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a SGRM or a checkpoint inhibitor in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical compositions of the invention can be delivered by transdermally, by a topical route, formulated as applicator sticks, solutions, suspensions, emulsions, gels, creams, ointments, pastes, jellies, paints, powders, and aerosols.

Lipid-based drug delivery systems include lipid solutions, lipid emulsions, lipid dispersions, self-emulsifying drug delivery systems (SEDDS) and self-microemuisifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The pharmaceutical compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the pharmaceutical compositions of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.*

13:293-306, 1996; Chonn, *Curr. Opin. Biotechnol.* 6:698-708, 1995; Ostro, *Am. J. Hosp. Pharm.* 46:1576-1587, 1989).

The pharmaceutical compositions of this disclosure may also comprise one or more adjuvants appropriate to the indicated route of administration. If administered orally, a compound used in the methods disclosed herein, such as a CIC or SGRM, may be mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

ii. Dosage

Pharmaceutical compositions suitable for administuration inlcude compositions, where the active ingredients, e.g., checkpoint inhibitors and SGRMs are contained in an amount effective to achieve their intended purpose. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compositions of the present invention employed, or the ester, salt or amide thereof, the pharmacokinetics of the composition, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions of the invention are preferably in unit dosage form. In such form the preparation is subdivided into unit doses containing appropriate quantities of the active component, a SGRM or a checkpoint inhibitor. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The dosage regimen of the checkpoint inhibitors or the SGRMs also takes into consideration pharmacokinetics parameters well known in the art, i.e., the rate of absorption, bioavailability, metabolism, clearance, and the like (see, e.g., Hidalgo-Aragones (1996) *J. Steroid Biochein. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacal.* 24:103-108; the latest Remington's, supra). The state of the art allows the clinician to determine the dosage regimen for each individual patient, SGRM and the checkpoint inhibitor based on the disease or condition treated.

The quantity of active component in a unit dose preparation may be varied or adjusted from 0.1 mg to 6000 mg, more typically 1.0 mg to 3000 mg, most typically 10 mg to 300 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents. Single or multiple administrations of compositions can be administered depending on the dosage and frequency as required and tolerated by the patient.

The compositions containing a checkpoint inhibitor should provide a sufficient quantity of the active component, i.e., the checkpoint inhibitor, when administered alone or in combination with a SGRM, to effectively treat the cancer, for example, in an amount being able to reduce tumor load or achieve other beneficial or desired clinical results related to cancer improvement. See section h, "evaluate improvements in reducing tumor loads". Thus, the dosage regimen may vary widely, but can be determined routinely using standard methods. In some cases, the pharmaceutical composition comprises a CIC and administration of a daily dose of about 1 to 2,000 mg, preferably between about 10 and about 1000 mg and most preferably between about 250 to 500 mg of the active ingredient, may be appropriate. The daily dose can be administered in one to four doses per day. Other dosing schedules include one dose per week and one dose per two-day cycle.

In some cases, the pharmaceutical compositions contain a CIA, and the dosage (of the active component) ranges from about 0.0001 to 100 mg/kg, and more usually 0.01 to 20 mg/kg, of the host body weight. For example dosages can be 0.3 mg/kg body weight, 1 mg/kg body weight, 3 mg/kg body weight, 5 mg/kg body weight, 10 mg/kg body weight or within the range of 0.1-20 mg/kg. An exemplary treatment regime entails administration once per day, once per week, twice a week, once every two weeks, once every three weeks, once every four weeks, once a month, once every 3 months or once every three to 6 months. In some cases, the treatment comprises administering a CIA according one of the aforementioned dosing regimens for a first period and another of the aforementioned dosing regimens for a second period. In some cases, the treatment discontinues for a period of time before the same or a different dosing regimen resumes. For example, a patient may be on a CIA dosing regimen for two weeks, off for a week, on for another two weeks, and so on. Preferred dosage regimens for a CIA of the invention include 0.1 mg/kg body weight, 0.3 mg/kg body weight, 2 mg/kg body weight, 3 mg/kg body weight or 10 mg/kg via intravenous administration, with the antibody being given using one of the following dosing schedules: (i)

every four weeks for six dosages, then every three months; (ii) every three weeks; 3 mg/kg body weight once followed by 1 mg/kg body weight every three weeks In some methods, two or more CIAs with different binding specificities are administered simultaneously, in which case the dosage of each antibody administered falls within the ranges indicated. CIAs are usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

The compositions containing a SGRM used in the combination therapy should provide a sufficient quantity of active agent to effectively potentiate the activity of the checkpoint inhibitor in treating cancer, for example, in an amount that, when combined with the therapeutic amount of a checkpoint inhibitor, can reduce tumor load or otherwise alleviate related cancer symptoms to a greater degree, or achieve greater beneficial or desired clinical results, as compared to the administration of the checkpoint inhibitor in the same therapeutic amount without the SGRM. In some cases, the compositions provide a SGRM at an amount that renders the tumor sensitive to the checkpoint inhibitor, i.e., a showing of a reduction of tumor load or other related clinical benefit that would not otherwise appear when the tumor is treated with the checkpoint inhibitor alone. Methods for evaluting tumor load reduction and other beneficial results are disclussed in section h "evaluate improvements in reducing tumor loads", infra. Thus, the dosage regimen may vary widely, depending on the route of administration and type of cancers to be treated, but can be determined routinely using standard methods. In some embodiments, the SGRM is administered once per month, twice per month, three times per month, every other week, once per week, twice per week, three times per week, four times per week, five times per week, six times per week, every other day, daily, twice a day, three times a day or more frequent.

In some cases, the daily oral dosage for the pharmaceutical composition containing a SGRM can be used for the methods disclosed herein, ranges from about 1 to about 2000 mg per day (mg/day). In some embodiments, the daily amount is from about 10 to 1000 mg/day, 50 to 500 mg/day, 100 to 300 mg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable compositions will be known or apparent to those skilled in the art and are described in more detail in such publications as Remington's, supra. See also Nieman. In "Receptor Mediated Antisteroid Action," Agarwal, et al., eds., De Ciruyter, N.Y. (1987). In some embodiments, the SGRM is CORT125281. In some embodiments, the SGRM is CORT 125134.

After a pharmaceutical composition including a SGRM or a checkpoint inhibitor of the invention has been formulated in an acceptable carrier, it can be placed in an appropriate container and labeled for treatment of an indicated condition. For administration of a SGRM or checkpoint inhibitor, such labeling would include, e.g, instructions concerning the amount, frequency and method of administration.

iii. Combination Therapy

The method disclosed herein involves a combination therapy of administering both a SGRM and a checkpoint inhibitor to a subject that suffers from a tumor load, which, in some cases, is due to the presence of a checkpoint inhibitor sensitive cancer. In some embodiments, the combination therapy involves administration of a checkpoint inhibitor and a SGRM sequentially in any order during the entire or portions of the treatment period.

In some cases, the SGRM and the checkpoint inhibitor are administered following the same or different dosing regimen. In some cases, the SGRM is administered following a scheduled regimen while the checkpoint inhibitor is administered intermittently. In some cases, the checkpoint inhibitor is administered following a scheduled regimen while the SGRM is administered intermittently. In some cases, both the SGRM and the checkpoint inhibitor are administered intermittently. In some embodiments, the SGRM is administered daily, and the checkpoint inhibitor, e.g., a checkpoint inhibitor, is administered weekly or biweekly.

In some cases, the SGRM and the checkpoint inhibitor are administered sequentially or simultaneously once or twice per month, three times per month, every other week, once per week, twice per week, three times per week, four times per week, five times per week, six times per week, every other day, daily, twice a day, three times a day or more frequent, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, the combination therapy includes co-administering a SGRM and a checkpoint inhibitor. In some embodiments, co-administration of a checkpoint inhibitor and a SGRM involves administering the two agents simultaneously or approximately simultaneously (e.g., within about 1, 5, 10,15, 20, or 30 minutes of each other).

iv. Duration

The duration of treatment with a SGRM and a checkpoint inhibitor to reduce tumor load can vary according to the severity of the condition in a subject and the subject's response to the combination therapy. In some embodiments, the SGRM and/or the checkpoint inhibitor can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72. weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. Generally, administration of a SGRM and/or a checkpoint inhibitor should be continued until the desired clinically significant reduction or amelioration is observed. Treatment with a SGRM and a checkpoint inhibitor in accordance with the invention may last for as long as two years or even longer. In some embodiments, the duration of the SGRM administration is the same as that of the checkpoint inhibitor. In some embodiments, the duration of SGRM administration is shorter or longer than that of the checkpoint inhibitor.

In some embodiments, administration of a SGRM or a checkpoint inhibitor is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

H. Evaluate Improvements in Reducing Tumor Loads

The combination therapy disclosed herein can reduce tumor load. Methods for measuring these responses are well-known to skilled artisans in the field of cancer therapy, e.g., as described in the Response Evaluation Criteria in Solid Tumors ("RECIST") guidelines, available at http://ctep.cancer.gov/protocolDevelopment/docs/recist_guideline.pdf.

In one approach, the tumor load is measured by assaying expression of tumor-specific genetic markers. This approach is especially useful for metastatic tumors or tumors that are not easily measurable, e.g., bone marrow cancer. A tumor-specific genetic marker is a protein or other molecule that is unique to cancer cells or is much more abundant in them as compared to non-cancer cells. For example, see WO 2006104474. Non-limiting examples of tumor-specific genetic markers include, alpha-fetoprotein (AFP) for liver cancer, beta-2-microglobulin (B2M) for multiple myeloma; beta-human chorionic gonadotropin (beta-hCG) for choriocarcinoma and germ cell tumors; CA19-9 for pancreatic cancer, gall bladder cancer, bile duct cancer, and gastric cancer; CA-125 and HE4 for ovarian cancer; carcinoembryonic antigen (CEA) for colorectal cancer; chromogranin A (CgA) for neuroendocrine tumor; fibrin/fibrinogen for bladder cancer; prostate-specific antigen (PSA) for prostate cancer; and thyroglobulin for thyroid cancer. See, http://www.cancer.gov/about-cancer/diagnosis-staging/diagnosis/tumor-markers-fact-sheet.

Methods of measuring the expression levels of a tumor-specific genetic marker are well known. In some embodiments, mRNA of the genentic marker is isolated from the blood sample or a tumor tissue and real-time reverse transcriptase-polymerase chain reaction (RT-PCR) is performed to quantify expression of the genetic marker. In some embodiments, western blots or immunohistochemistry analysis are performed to evaluate the protein expression of the tumor-specific genetic marker. Typically the levels of the tumor-specific genetic marker are measured in multiple samples taken over time of the combination therapy of the invention, and a decrease in levels correlates with a reduction in tumor load.

In another approach, the reduction of tumor load by the combination therapy disclosed herein is shown by a reduction in tumor size or a reduction of amount of cancer in the body. Measuring tumor size is typically achieved by imaging-based techniques. For example, computed tomography (CT) scan can provide accurate and reliable anatomic information about not only tumor shrinkage or growth but also progression of disease by identifying either growth in existing lesions or the development of new lesions or tumor metastasis.

In another approach, a reduction of tumor load can be assessed by functional and metabolic imaging techniques. These techniques can provide earlier assessment of therapy response by observing alterations in perfusion, oxygenation and metabolism. For example, $^{18}$F-FDG PET uses radiolabelled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

A patient receiving the combination therapy disclosed herein may exhibit varying degrees of tumor load reduction. In some cases, a patient can exhibit a Complete Response (CR), also referred to as "no evidence of disease (NED)". CR means all detectable tumor has disappeared as indicated by tests, physical exams and scans. In some cases, a patient receiving the combination therapy disclosed herein can experience a Partial Response (PR), which roughly corresponds to at least a 50% decrease in the total tumor volume but with evidence of some residual disease still remaining. In some cases the residual disease in a deep partial response may actually be dead tumor or scar so that a few patients classified as having a PR may actually have a CR. Also many patients who show shrinkage during treatment show further shrinkage with continued treatment and may achieve a CR. In some cases, a patient receiving the combination therapy can experience a Minor Response (MR), which roughly means a small amount of shrinkage that is more than 25% of total tumor volume but less than the 50% that would make it a PR. In some cases, a patient receiving the combination therapy can exhibit Stable Disease (SD), which means the tumors stay roughly the same size, but can include either a small amount of growth (typically less than 20 or 25%) or a small amount of shrinkage (Anything less than a PR unless minor responses are broken out. If so, then SD is defined as typically less 25%).

Desired beneficial or desired clinical results from the combination therapy may also include e.g., reduced (i.e., slowing to some extent and/or stop) cancer cell infiltration into peripheral organs; inhibit (i.e., slow to some extent and/or stop) tumor metastasis; increased response rates (RR); increased duration of response; relieved to some extent one or more of the symptoms associated with the cancer; decreased dose of other medications required to treat the disease; delayed progression of the disease; and/or prolonged survival of patients and/or improved quality of life. Methods for evaluating these effects are well known and/or disclosed in, e.g., http://cancerguide.org/endpoints.html and RECIST guidelines, supra.

All patents, patent applications, and publications discussed herein are hereby incorporated by reference in their entireties.

EXAMPLES

Example 1

HEPG2 Tyrosine Aminotransferase (TAT) Assay

The following protocol describes an assay for measuring induction of TAT by dexamethasone in HepG2 cells (a human liver hepatocellular carcinoma cell line; ECACC, UK). HepG2 cells are cultured using MEME media supplemented with 10% (v/v) foetal bovine serum; 2 mM L-glutamine and 1% (v/v) NEAA at 37° C., 5%/95% (v/v) $CO_2$/air. The HepG2 cells are then be counted and adjusted to yield a density of 0.125×10$^6$ cells/ml in RPMI 1640 without phenol red, 10% (v/v) charcoal stripped FBS, 2 mM L-glutamine and seeded at 25,000 cells/well in 200% μinto 96 well, sterile, tissue culture micro titre plates, and incubated at 37° C., 5% CO$_2$ for 24 hours.

Growth media are then removed and replaced with assay media {RPMI 1640 without phenol red, 2 mM L-glutamine+10 μM forskolin}. Test compounds are then be screened against a challenge of 100 nM dexamethasone. Compounds are then be serially half log diluted in 100% (v/v) dimethylsupfoxide from a 10 mM stock. Then an 8-point half-log dilution curve are generated followed by a 1:100 dilution into assay media to give a 10× final assay of the compound concentration, this results in final assay of the compound concentration that ranged 10 to 0.003 μM in 0.1% (v/v) dimethylsulfoxide.

Test compounds are pre-incubated with cells in microtitre plates for 30 minutes at 37° C., 5/95 (v/v) CO$_2$/air, before the addition of 100 nM dexamethasone and then subsequently for 20 hours to allow optimal TAT induction. HepG2 cells are then lysed with 30 μl of cell lysis buffer containing a protease inhibitor cocktail for 15 minutes at 4° C., 155 μl of substrate mixture can then be added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction can be terminated by the addition of 15 μl of 10M aqueous potassium hydroxide solution, and the plates incubated for a further 30 minutes at 37° C. The TAT activity product can be measured by absorbance at λ 340 nm.

IC$_{50}$ values can be calculated by plotting % inhibition (normalised to 100 nM dexamethasone TAT stimulation) v. compound concentration and fitting the data to a 4 parameter logistic equation. IC$_{50}$ values can converted to Ki (equilibrium dissociation constant) using the Cheng and Prusoff equation, assuming the antagonists were competitive inhibitors with respect to dexamethasone.

Example 2

Quantify the GR Expression in Cancer Types

Formalin-fixed paraffin-embedded (FFPE) tumor tissue sections of 4-5 μm thickness are cut onto positively charged slides (Fisher ProbeOn Plus™, Thermo Fisher Scientific), baked at 65° C. (dry heat) for 1 hour less than 1 week before use, deparaffinized in four changes of 100% xylene, and rehydrated with a graded ethanol series (100%, 70%, 30%) to distilled water.

Prepared slides are incubated for 20 minutes at 0.98° C. in Citra Plus Target Retrieval Solution (BioGenex [Cat #: HK #080-9K], Fremont, Calif., USA), using a commercial steamer as the heat source (Black and Decker HS1000 model steamer; Black and Decker, Baltimore, Md., USA). After cooling for 5 minutes, automated staining is performed using a TechMate™ 500 or 1000 automated IMC staining platform (Roche Diagnostics, Oro Valley, Ariz., USA) and WorkMate™ software, version 3.96. This automated platform uses a capillary gap process29 for all reagent changes, including antibody incubation, detection steps up to and including counterstaining, and intervening washes. All procedures are carried out at room temperature (25° C.). Following a 15-minute incubation with a protein serum block (QualTek Proprietary), slides are incubated with the anti-GR antibody, clone D8H2 (Cell Signaling Technology [#3660S]) at a concentration of 1:1,750 in a primary antibody diluent (QualTek Proprietary) for 1 hour.

The Rabbit Polink2+ HRP (horseradish peroxidase) reagents kit (Golden Bridge International [GBI], Cat #: D39-110, Los Angeles, Calif., USA), which is biotin-independent and reduces the potential for background or non-specific staining from endogenous biotin, is used for primary antibody detection. The steps included are a 25-minute incubation with Rabbit Polink2+ secondary, a 7.5-minute peroxidase blocking step (3% USP H2O2, with ~0.02% v/v Tween-20 added), a 25-minute incubation with Rabbit Polink2+ HRP conjugated polymer, and a 15-minute incubation with GBI (Cat #: C09-100) 3,3'-diaminobenzidine (DAB) chromogen. Between all incubation steps, slides are extensively washed with tris-buffered saline containing 0.02% v/v Tween®-20 detergent (TBST) (Thermo Fisher Scientific). The slides are counterstained with hematoxylin for 1 minute, rinsed in distilled water, dehydrated off platform in an ethanol series (95%, 100%) and four changes of 100% xylene, and permanently sealed with coverslips (Cytoseal™ XYL mounting media, Thermo Fisher Scientific).

A percent score is used to semiquantitatively assess tumor GR expression in samples with at least 100 viable invasive carcinoma cells. The intensity of nuclei staining is reported based on the H-score method using 0 for negative staining, 1+ for weak staining, 2+ for moderate staining, and 3+ for strong staining. The H-score is calculated by multiplying the staining intensity by the proportion of cells with that intensity. For example, a sample with 20% of cells having weak staining and 2% of cells having moderate staining would have an H-score of 24 [(20×1)+(2×2)=24]. For this assay, GR positivity is defined as 10% nuclear staining of tumor cells at any intensity A board-certified pathologist scores nuclear tumor staining in the total area of viable tissue section available; areas of cytoplasmic or stromal staining, in situ carcinoma, necrosis, or obviously poorly fixed areas of tissue are not evaluated.

Example 3

Reducing Tumor Growth Using the Combination Therapy of CORT 125134 AND ANTI PD-1

Suspensions of mouse MC38 cancer cells were injected subcutaneously into the left flank of 5-6 week old immunocompetent female mice (C57BL/6), 1 million cells per mouse. Tumors were allowed to grow until they reach a volume of 100 mm$^3$. Mice were then grouped into three groups, ten (10) per group. Group I was dosed with the anti-PD-1 vehicle (PBS, 10 ml/kg) i. p. twice a week and the CORT125134 vehicle p.o. (10% DMSO, 0.1% Tween 80 and 89.9% HPMC (0.5%), 10 ml/kg) daily. Group II was dosed with the mouse anti PD-1 antibody (clone RPM1-14, 10 mg/kg) i. p, twice a week. Group III was dosed with the mouse anti PD-1 antibody (clone RPM1-14, 10 mg/kg) i. p. twice a week and CORT125134 (a SGRM) (30 mg/kg) orally on a daily basis.

The longest (L) and shortest (S) diameters of the tumors were measured three times a week with electronic calipers and tumor volume was calculated using the formula for an ellipsoid sphere: S$^2$×L×(0.5). The tumor growth data are shown in FIG. 1, in which the mean tumor volume as compared to the mean pre-dosing tumor volume for each group of mice is plotted against the number of days of tumor growth since initiation of the treatment. The result shows that the combination of anti PD-1 and CORT125134 is superior to both the anti PD-1 group and the vehicle group in reducing tumor growth.

Example 4

Reducing Tumor Growth Using the Combination Therapy of CORT125281 and Anti PD-1

Suspensions of mouse A20 cancer cells were injected subcutaneously into the left flank of 5-6 week old immunocompetent female mice (C57BL/6), ½ million cells per mouse. Tumors were allowed to grow until they reached a volume of 100 mm³. Mice were then grouped into three groups, ten (10) per group. Group I was dosed with the anti-PD-1 vehicle (PBS, 10 ml/kg) i. p. twice a week and the CORT125281 vehicle p.o. (10% DMSO, 0.1% Tween 80 and 89.9% HPMC (0.5%), 10 ml/kg) daily. Group II was dosed with the mouse anti PD-1 antibody (clone RPM1-14, 10 mg/kg) i. p. twice a week. Group III was dosed with the mouse anti PD-1 antibody (clone RPM1-14, 10 mg/kg) i. p. twice a week and CORT125281 (a SGRM) (30 mg/kg) orally on a daily basis.

Figure 2:
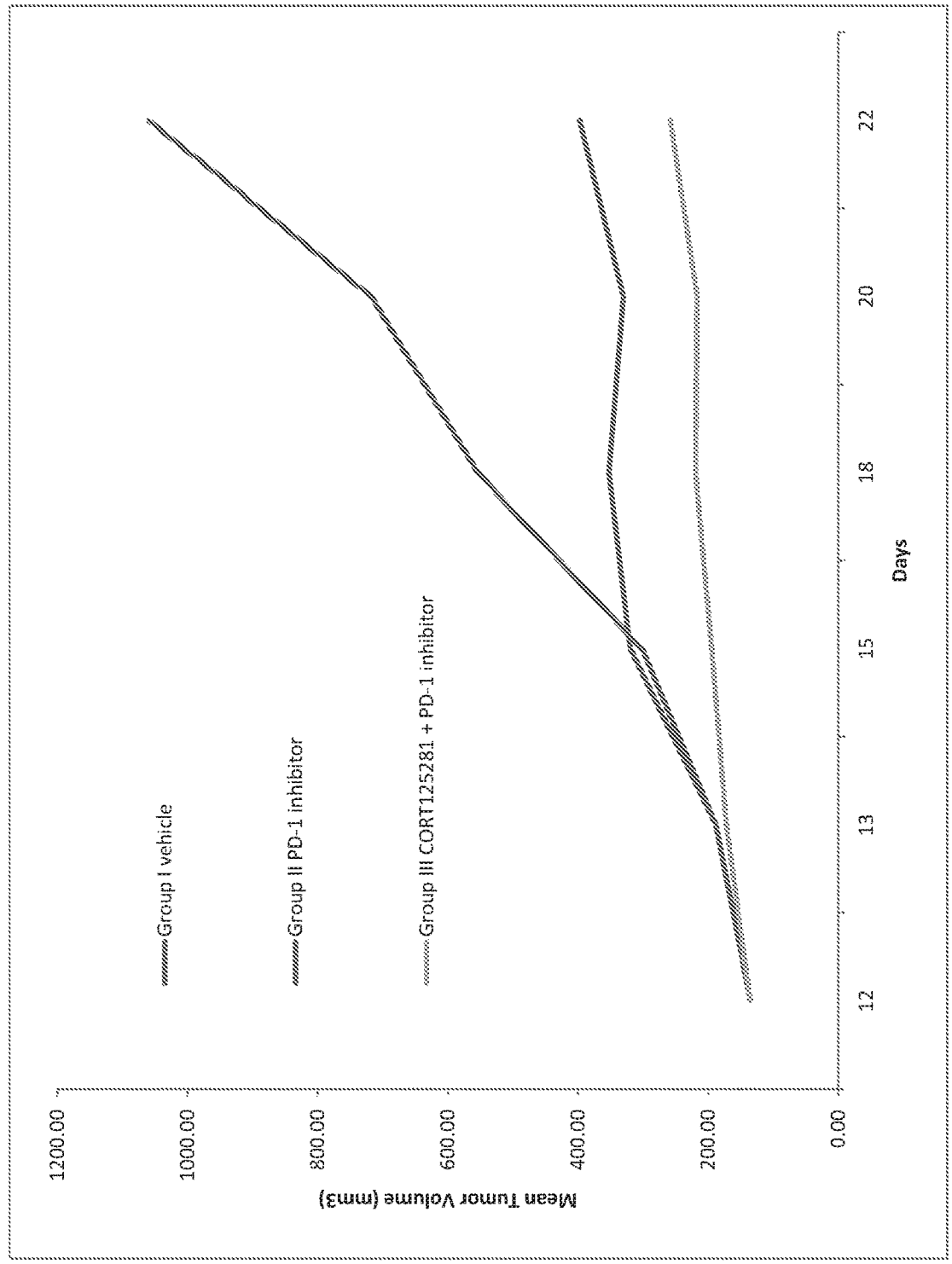
FIG. 2 shows the mean tumor volume for each group of ten mice plotted against the number of days of tumor growth since initiation of the treatment. Group I mice were dosed with the anti-PD-1 vehicle and the CORT125281 vehicle; Group II mice were dosed with mouse anti PD-1 antibody; and Group III mice were dosed with mouse anti PD-1 antibody and CORT125281. The combination of anti PD-1 and CORT125281 is superior to both the anti PD-1 group and the vehicle group in reducing tumor growth.

The longest (L) and shortest (S) diameters of the tumors were measured three times a week with electronic calipers and tumor volume was calculated using the formula for an ellipsoid sphere: $S^2 \times L \times (0.5)$. The tumor growth data are shown in FIG. 2, in which the mean tumor volume for each group of mice is plotted against the number of days of tumor growth since initiation of the treatment. The result shows that the combination of anti PD-1 and CORT125281 is superior to both the anti PD-1 group and the vehicle group in reducing tumor growth.

Example 5

Reducing Tumor Growth Using the Combination Therapy of CORT125134 or CORT125281 and Anti CTLA4

Suspensions of mouse CT26 cancer cells were injected subcutaneously into the left flank of 6-7 week old immunocompetent female mice (C57BL/6), ½ million cells per mouse. Tumors were allowed to grow until they reached a volume of 50-100 mm³. Mice were then grouped into three groups, ten (10) per group. Group I was dosed with the anti-CTLA4 vehicle (PBS, 10 ml/kg) i. p. twice a week and the CORT125134 vehicle p.o. (10% DMSO, 0.1% Tween 80 and 89.9% HPMC (0.5%), 10 ml/kg) daily. Group II was dosed with the mouse anti CTLA4 antibody (clone 9D9, 10 mg/kg) i. p. twice a week. Group III was dosed with the mouse anti CTLA4 antibody (clone 9D9, 10 mg/kg) i. p. twice a week and CORT125134 (a SGRM) (30 mg/kg) orally on a daily basis. Group IV was dosed with the mouse anti CTLA4 antibody (clone 9D9, 10 mg/kg) i. p. twice a week and CORT125281 (a SGRM) (30 mg/kg) orally on a daily basis.

Figure 3:
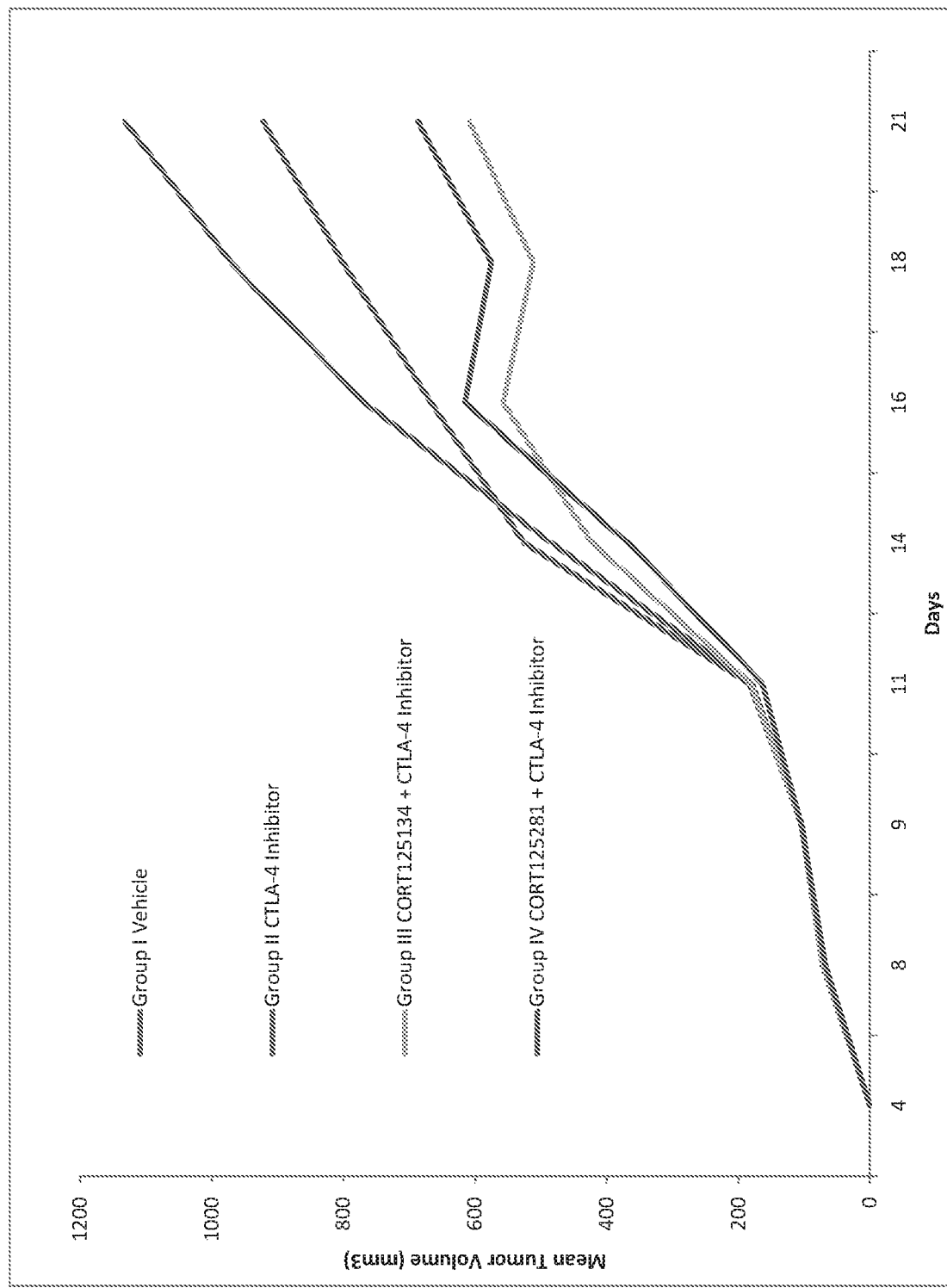
FIG. 3 shows the mean tumor volume for each group of ten mice plotted against the number of days of tumor growth since initiation of the treatment. Group I mice were dosed with the anti-CTLA4 vehicle and the CORT125134 vehicle; Group II mice were dosed with the mouse anti CTLA4 antibody; Group III mice were dosed with mouse anti CTLA4 antibody and CORT125134; Group IV mice were dosed with mouse anti CTLA4 antibody and CORT125281. The combination of anti CTLA4 with CORT125134 and the combination of anti CTLA4 with CORT125281 were each superior to both the anti CTLA4 group and the vehicle group in reducing tumor growth.

The longest (L) and shortest (S) diameters of the tumors were measured three times a week with electronic calipers and tumor volume was calculated using the formula for an ellipsoid sphere: $S^2 \times L \times (0.5)$. The tumor growth data are shown in FIG. 3, in which the mean tumor volume for each group is plotted against the number of days of tumor growth since initiation of the treatment. The result shows that the combination of anti CTLA4 with CORT125134 and the combination of anti CTLA4 with CORT125281 are superior to both the anti CTLA4 group and the vehicle group in reducing tumor growth.

Example 6

Treating a Breast Cancer Patient with the Combination Therapy

A patient suffering from breast cancer is treated with prembrolizumab at a dose of 3 mg/kg every 2 weeks and CORT125134 at a dose of 200 mg once a day for eight weeks. Her tumor load is monitored using enhanced magnetic resonance imaging before, during and after the treatment. The imaging result indicate that the size of the tumor has gradually decreased, and the reduction is more than 20% at the end of the treatment period.

What is claimed is:

1. A method for reducing tumor load in a patient hosting a tumor, the method effective to potentiate the activity of the antibody checkpoint inhibitor effective to provide superior tumor load reduction as compared to the tumor load reduction that would be provided by said antibody checkpoint inhibitor alone, comprising:

administering to said patient hosting a tumor a therapeutic amount of the antibody checkpoint inhibitor and between about 10 milligrams (mg) to about 1000 mg per day of a selective glucocorticoid receptor antagonist (SGRA) effective to provide tumor load reduction at least 10% greater than the tumor load reduction provided by the antibody checkpoint inhibitor alone, wherein the antibody checkpoint inhibitor is selected from lambrolizumab, nivolumab, AMP-224, pidilizumab, ipilimumab, tremelimumab, MEDI4736, MPDL3280A and BMS-936559 (MDX-1105), wherein said SGRA is a compound that has a heteroaryl-ketone fused azadecalin backbone or an octahydro fused azadecalin backbone, and that binds the glucocorticoid receptor (GR) with a GR binding affinity that is at least ten-fold greater than its binding affinity for the mineralocorticoid receptor, said GR binding being able to inhibit GR-mediated activity, and where the SGRA is administered in an amount effective to potentiate the activity of the antibody checkpoint inhibitor effective to provide at least 10% greater tumor load reduction in the patient as compared to the tumor load reduction provided by the antibody checkpoint inhibitor alone.

2. The method of claim 1, wherein the tumor load is due to the presence of a checkpoint inhibitor-sensitive tumor.

3. The method of claim 1 wherein the checkpoint inhibitor is an antibody effective against PD-1 selected from lambrolizumab, nivolumab, AMP-224, and pidilizumab.

4. The method of claim 1 wherein the checkpoint inhibitor is an antibody effective against CTLA-4 selected from ipilimumab and tremelimumab.

5. The method of claim 1 wherein the checkpoint inhibitor is an antibody effective against PD-L1 or PD-L2 selected from MEDI4736, MPDL3280A and BMS-936559 (MDX-1105).

6. The method of claim 1 wherein the SGRA is CORT125134

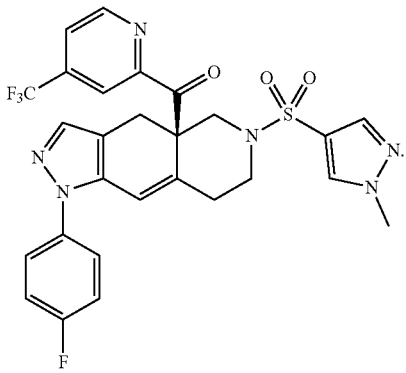

7. The method of claim 1, wherein the SGRA is CORT125281

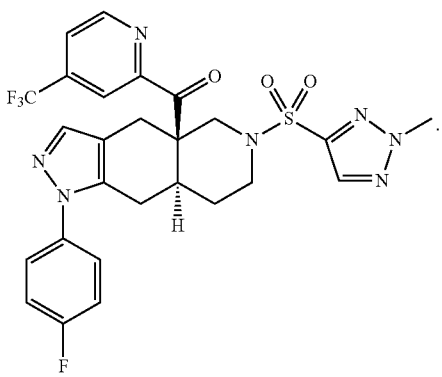 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

8. The method of claim 1 wherein the cancer expresses the glucocorticoid receptor (GR+).

9. The method of claim 1 wherein the cancer is a GR+ cancer and wherein the cancer is selected from the group consisting of breast cancer, prostate cancer, Melanoma, Sarcoma, Renal cell cancer, Head and Neck cancer, Hepatocellular cancer, Glioblastoma, Cervical cancer, neuroendocrine cancer, Bladder cancer, Prostate cancer, Esophageal cancer, mesothelioma, Lung cancer, Ovarian cancer, Pancreas cancer, Gall bladder cancer, Gastric cancer, Endometrial cancer, and colon cancer.

10. The method of claim 7 wherein the SGRA is CORT125281 and the checkpoint inhibitor is an antibody effective against PD-1 selected from the group of anti-PD-1 antibody checkpoint inhibitors consisting of lambrolizumab, nivolumab, AMP-224, and pidilizumab.

11. The method of claim 6 wherein the SGRA is CORT125134 and the checkpoint inhibitor is an antibody effective against PD-1 selected from the group of anti-PD-1 antibody checkpoint inhibitors consisting of lambrolizumab, nivolumab, AMP-224, and pidilizumab.

12. The method of claim 1 wherein the SGRA is CORT125281 or CORT125134 and the checkpoint inhibitor is an antibody effective against CTLA-4 selected from the group of anti-CTLA-4 antibody checkpoint inhibitors consisting of ipilimumab and tremelimumab.

13. The method of claim 1 wherein the SGRA is CORT125281 or CORT125134 and the checkpoint inhibitor is an antibody effective against PDL-1 or PDL-2 selected from the group of anti-PD-L1 or anti-PD-L2 antibody checkpoint inhibitors consisting of MEDI4736, MPDL3280A and BMS-936559 (MDX-1105).

* * * * *

UNITED STATES PATENT AND TRADEMARK OFFICE
CERTIFICATE OF CORRECTION

PATENT NO. : 10,980,797 B2
APPLICATION NO. : 16/080617
DATED : April 20, 2021
INVENTOR(S) : Hazel Hunt It is certified that error appears in the above-identified patent and that said Letters Patent is hereby corrected as shown below:

In the Claims

In Column 48, Line 24, Claim 1, please delete "activity of the" and replace with --activity of an--

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*